US006706767B2

(12) United States Patent
Saxena et al.

(10) Patent No.: US 6,706,767 B2
(45) Date of Patent: Mar. 16, 2004

(54) THERAPEUTICS FOR CHEMOKINE MEDIATED DISEASES

(75) Inventors: Geeta Saxena, Vancouver (CA); Christopher R. Tudan, Vancouver (CA); Hassan Salari, Delta (CA)

(73) Assignee: Chemokine Therapeutics Corporation, Vancouver (CA)

( * ) Notice: Subject to any disclaimer, the term of this patent is extended or adjusted under 35 U.S.C. 154(b) by 0 days.

(21) Appl. No.: 09/767,378

(22) Filed: Jan. 22, 2001

(65) Prior Publication Data

US 2003/0069265 A1 Apr. 10, 2003

(30) Foreign Application Priority Data

Dec. 6, 2000 (CA) .............................................. 2330350

(51) Int. Cl.⁷ ............................................ A61K 31/122

(52) U.S. Cl. ..................................................... 514/680

(58) Field of Search ........................................ 514/680

(56) References Cited

U.S. PATENT DOCUMENTS 2,956,065 A  * 10/1960  DeWalt et al. .............. 260/396

FOREIGN PATENT DOCUMENTS

| EP | 0 240 859 A | 10/1987 |
| GB | 2 186 570 A | 8/1987 |
| WO | WO 98/27975 | 7/1998 |
| WO | WO 99/11624 | 3/1999 |
| WO | WO 99/42464 | 8/1999 |
| WO | WO 00/63179 | 10/2000 |
| WO | WO 01/42219 | 6/2001 |
| WO | WO 01/46125 | 6/2001 |
| WO | WO 01/90077 | 11/2001 |

OTHER PUBLICATIONS

Acsadi, G. et al, (1991) *Nature*, vol. 352, 815–818.
Aiuti, A. et al, (1997) *J. Exp. Med.*, vol. 185–1, 111–120.
Aiuti, A. et al, (1999) *Eur. J. Immunol.*, vol. 29, 1823–1831.
Alkhatib, G et al, (1996) *Science*, vol. 272, 1955–1958.
Allen, M. et al, (2000) *J. Biomolecular Screening*, vol. 5 No. 2, 63–69.
Alleva, D. et al, (1998) *J. Immunol.*, vol. 161–12, 6878–6884.
Anderlini, P. et al, (1997) *Blood* vol. 90 No. 3, 903–908.
Anderson, W., et al, (2000) *Science*, vol. 288, 627–629.
Arenzana–Selsdedos, F. et al, (1996) *Nature*, vol. 383, 400.
Armentano, D., et al, (1990) *Proc. Natl. Acad. Sci.*, vol. 87, 6141–6145.
Ausubel et al, (1995) *Current Protocols in Mol. Biol., Supp.* vol. 36, 9.10.1–9.14.6.
Avenarius, H. et al, (1993) *Inter. J. Hematology*, vol. 58, 189–196.
Baggiolini, M. (1998) *Nature*, vol. 392, 565–568.

Baird, A. et al, (1999) *Current Opinion in Immunology*, vol. 11, 157–166.
Balasa, B. et al, (1997) *J. Exp. Med.*, vol. 186, 385–391.
Baldari, J. et al (1987) *EMBO Journal*, vol. 6 No. 1, 229–234.
Barbier, J. et al, (1997) *J. Med. Chem.*, vol. 40 No. 9, 1373–1380.
Barbier, J. et al, (2000) *Biochemistry 2000*, vol. 39 No. 47, 14522–14530.
Barnes, D. et al, (1998) *J. Clin. Invest*, vol. 101 No. 12, 2910–2919.
Berkner, K., (1988) *Biotechniques*, vol. 6 No. 7, 616–628.
Blease, K. et al, (2000) *J. Immunol.*, vol. 165, 1564–1572.
Bleul, C. et al, (1996) *J. Exp. Med.*, vol. 184, 1101–1109.
Bleul, C. et al, (1996) *Nature*, vol. 382, 829–832.
Brandt, J. et al, (1990) *J. Clin. Invest.*, vol. 86, 932–941.
Brandt, J. et al, (1992) *Blood*, vol. 79 No. 3, 634–641.
Brandt, J. et al, (1998) *J. Clin. Invest.*, vol. 82, 1017–1027.
Buckley, C. et al, (2000) *J. Immunol.*, vol. 165, 3423–3429.
Burt, R., (1999) *Stem Cells*, vol. 17, No. 6, 366–372.
Campbell, J. et al, (1998) *Science*, vol. 279, 381–383.
Carr, M. et al, (1994) *Proc. Natl. Acad. Sci.*, vol. 91, 3652–3656.
Cashman, J. et al, (1999) *Blood*, vol. 94 No. 11, 3722–3729.
Cavazzana–Calvo, M. et al, (2000) *Science*, vol. 288, 669–672.
Charo, I. et al, (1994) *Proc. Natl. Acad. Sci.*, vol. 91, 2752–2756.
Choe, H. et al, (1996) *Cell*, vol. 85, 1135–1148.
Chowdhury, J. et al, (1991) *Science*, vol. 254, 1802–1805.
Clapp, W. et al, (1991) *Blood*, vol. 78 No. 4, 1132–1139.
Clark–Lewis, I. et al, (1994) *J. Biol. Chem.*, vol. 269 No. 23, 16075–16081.
Cocchi, F. et al (1995) *Science*, vol. 270, 1811–1815.
Combadiere, C. et al, (1995) *J. Biol. Chem.*, vol. 270, 16491–16494.
Conti, J. et al, (1992) *Cancer*, vol. 70 No. 11, 2699–2702.
Cristiano, R. et al, (1993) *Proc. Natl. Acad. Sci.*, vol. 90, 2122–2126.

(List continued on next page.)

Primary Examiner—Phyllis G. Spivack
(74) Attorney, Agent, or Firm—Bret E. Field; Bozicevic, Field & Francis

(57) ABSTRACT

The invention provides therapeutic and biological uses of chemokine-receptor-binding compounds including uses in the treatment of disease states mediated by chemokines. The relevant chemokines may for example be monocyte chemoattractant protein-one (MCP-1) or interleukin-8 (IL-8), and the relevant chemokine receptors may for example be corresponding chemokine receptors (CCR-2, CCR-4, CXCR-1, and CXCR-2). In one aspect, the invention provides for the use of phenanthrene-9,10-dione in the treatment of multiple sclerosis.

4 Claims, 12 Drawing Sheets

OTHER PUBLICATIONS

Crump, M. et al, (1997) *EMBO Journal*, vol. 16 No. 23, 6996–7007.
Curiel, D. et al, (1991) *Proc. Natl. Acad. Sci.*, vol. 88, 8850–8854.
Cushing, S. et al, (1990) *Proc. Natl. Acad. Sci.*, vol. 87, 5134–5138.
Cwirla, S. et al, (1997) *Science*, vol. 276, 1696–1699.
Dai, Y. et al, (1992) *Proc. Natl. Acad. Sci.*, vol. 89, 10892–10895.
Danos, O. et al, (1988) *Proc. Natl. Acad. Sci.*, vol. 85, 6460–6464.
Demirer, T. et al, (1996) *Stem Cells*, vol. 14, 106–116.
Deng, H. et al, (1996) *Nature*, vol. 381, 661–666.
Dhib–Jalbut, S. et al (1996) *Journal of Interferon and Cytokine Research*, vol. 16, 195–200.
Di Salvo, J. et al, (2000) *Eur. J. Pharm.*, vol. 409, 143–154.
Doranz, B. et al (1996) *Cell, vol.* 85, 1149–1158.
Dragic, T. et al, (1996) *Nature*, vol. 381, 667–673.
Dunican, A. et al, (2000) *Shock*, vol. 13 No. 3, 244–250.
Durig, J. et al, (2000) *Leukemia*, vol. 14, 1652–1660.
Eglitis, M. et al, (1985) *Science*, vol. 230, 1395–1398.
Elisseeva, E. et al, (2000) *J. Biol. Chem.*, vol. 275 No. 35, 26799–26805.
Elseviers, M. et al, (1998) *Biochem. and Biophys. Research Comm.*, vol. 154 No. 2, 515–521.
Federsppiel, B. et al, (1993) *Genomics*, vol. 16, 707–712.
Feng, Y. et al, (1996) *Science*, vol. 272, 872–877.
Ferry, N. et al, (1991) *Proc. Natl. Acad. Sci.*, vol. 88, 8377–8381.
Fletcher, F. et al, (1990) *Blood*, vol. 76 No. 6, 1098–1103.
Flotte, T. et al, (1992) *Am. J. Respir. Cell Mol. Biol.*, Vol 7, 349–356.
Flotte, T. et al, (1993) *J. Biol. Chem.*, vol. 268 No. 5, 3781–3790.
Furuichi, K. et al, (2000) *Am. J. Nephrol.*, vol. 20, 291–299.
Gimbrone, M. et al, (1989) *Science*, vol. 246, 1601–1603.
Giralt, S. et al, (1997) *Blood*, vol. 89 No. 12, 4531–4536.
Gong, J. et al, (1996) *J. Biol. Chem.*, vol. 271 No. 18, 10521–10527.
Gupta, S. et al, (1998) *J. Biol. Chem.*, vol. 273 No. 7, 4282–4287.
Haas, R. et al, (1992) *Bone Marrow Transplantation*, vol. 9, 459–465.
Hamada, T. et al, (1998) *J. Exp. Med.*, vol. 188 No. 3, 539–548.
Hartung, H. et al, (1990) *Ann. Neurol.*, vol. S57, S57 –S63.
Hermonat, P. et al, (1984) *Proc. Natl. Acad. Sci.*, vol. 81, 6466–6470.
Herz, J. et al, (1993) *Proc. Natl. Acad. Sci.*, vol. 90, 2812–2816.
Heveker, N. et al, (1998) *Current Biology*, vol. 8, 369–376.
Ho, A. et al, (1993) *Leukemia*, vol. 7 No. 11, 1738–1746.
Hodohara, K. et al, (2000) *Blood*, vol. 95 No. 3, 769–775.
Heveker, N. et al. (1998) Current Biology, vol. 8, 369–376.
Holmes, W. et al, (1991) *Science*, vol. 253 No. 50, 1278–1280.
Hooper, D. et al, (1998) *Proc. Natl. Acad. Sci.*, vol. 95, 675–680.
Horuk, R. et al, (2001) *J. Biol. Chem.*, vol. 276 No. 6, 4199–4204.
Huang, S. et al, (1992) *Nature*, vol. 360, 745–749.
Huber, A. et al, (1991) *Science*, vol. 254, 99–102.

Huber, B. et al, (1991) *Proc. Natl. Acad. Sci.*, vol. 88, 8039–8043.
Hwu, P. et al, (1993) *J. Immunol.*, vol. 150, 4104–4115.
IFNB Mutiple Sclerosis Study Group, (1993) *Neurology* vol. 43, 655–661.
Ikebuchi, K. et al, (2001) *Nat. Acad. Sci.*, vol. 85, No. 10, 3445–3449.
Imai, T. et al, (1997) *J. Biol. Chem.*, vol. 272 No. 23, 15036–15042.
Imai, T. et al, (1998) *J. Biol. Chem.*, vol. 273 No. 3, 1764–1768.
Jones, S. et al, (1997) *J. Biol. Chem.*, vol. 272 No. 26, 16166–16169.
Kates, S. et al, (1993) *Analytical Biochemistry*, vol. 212, 303–310.
Kaufman R. et al, (1987) *EMBO Journal*, vol. 6 No. 1, 187–193.
Kawachi, Y. et al, (1996) *Brit. J. Hematology*, vol. 94, 413–416.
Kay, M. et al, (1992) *Human Gene Therapy*, vol. 3, 647–647.
Kessinger, A. et al, (1989) *Bone Marrow Transplantation*, No. 4, 643–646.
Kim, C. et al, (1999) *J. Leukocyte Biology*, vol. 65, 6–15.
Kitaura, M. et al, (1996) *J. Biol. Chem.*, vol. 271 No. 13, 7725–7730.
Koch, A. et al, (1992) *Science*, vol. 258, 1798–1801.
Kowalska, M. et al, (2000) *Blood*, vol. 96, No. 1, 50–57.
Kramer, W. et al, (1992) *J. Biol. Chem.*, vol. 267 No. 26, 18598–18604.
Kume, A. et al, (1999) *Int. J. Hematology*, vol. 69, 227–233.
Kurjan, J. et al, (1982) *Cell*, vol. 30, 933–943.
Kuroiwa, M. et al, (1996) *Int. J. Hematology*, vol. 63, 311–316.
Lasky, L. et al, (1981) *Transfusion*, vol. 21 No. 3, 247–260.
Lataillade, J. et al, (2000) *Blood*, vol. 95 No. 3, 756–768.
Law. P., (1983) *Exp. Hematol.*, vol. 11 No. 5, 351–357.
Le Chevalier, T., (1994) *Eur. J. Cancer*, vol. 30A No. 3, 410–412.
Leary, A. et al, (1988) *Blood*, vol. 71 No. 6, 1759–1763.
Lemarchand, P. et al, (1992) *Nat. Acad. Sci.*, vol. 89 No. 4, 6482–6486.
Lin, T. et al, (2000) *J. Immunol.*, vol. 165, 211–220.
Loetscher, M. et al, (1994) *J. Biol. Chem.*, vol. 269 No. 1, 232–237.
Loetscher, P. et al, (1994) *FASEB J.*, vol. 8, 1055–1060.
Loetscher, P. et al, (1998) *J. Biol. Chem.*, vol. 273 No. 35, 22279–22283.
Lohrmann, H. et al, (1978) *B. J. Haematol.*, vol. 40, 369–381.
Lombart, H. et al, (1994) *J. Org. Chem.*, vol. 59, 6147–6149.
Luckow, V. et al, (1989) *Virology*, vol. 170, 31–39.
Lukacs, N. et al, (1997) *J. Immunol.*, vol. 158, 4398–4404.
Luo, J. et al, (1999) *Biochemical and Biophysical Research Communications*, vol. 264, 42–47.
Marshall, G. et al, (1993) *Tetrahedron*, vol. 49 No. 17, 3547–3558.
McLaughlin, S. et al, (1988) *J. Virology*, vol. 62 No. 6, 1963–1973.
Miller, D., (1990) *Blood* vol. 76 No. 2, 271–278.
Moss, J., (1995) *American Chem. Soc.*, Chapter 18, 423–448.
Moss, T. et al, (1990) *Blood*, vol. 76 No. 9, 1879–1883.
Murphy, P. et al, (1991) *Science*, vol. 258, 1280–1283.

Muzyczka, N., (1992) *Current Topics in Microbiol. and Immunol.*, vol. 158, 98–129.
Myers, S. et al, (1995) *J. Biol. Chem.*, vol. 270 No. 11, 5786–5792.
Nagai, U. et al, (1993) *Tetrahedron*, vol. 49 No. 17, 3577–3592.
Nagasawa, T. et al, (1994) *Proc. Natl. Acad. Sci.*, vol. 91, 2305–2309.
Nagasawa, T. et al, (1996) *Nature*, vol. 382, 635–638.
Nagasawa, T. et al, (1996) *Proc. Natl. Acad. Sci.*, vol. 93, 14726–14729.
Neote, K. et al, (1993) *Cell*, vol. 72, 415–425.
Ng, H. et al, (1999) *J. Med. Chem.*, vol. 42, 4680–4694.
Oberlin, E. et al, (1996) *Nature*, vol. 382, 833–835.
Peled, A. et al, (1999) *Science*, vol. 283, 845–848.
Pettengell, R. et al, (1993) *Blood*, vol. 82 No. 7, 2239–2248.
Quantin, B. et al, (1992) *Proc. Natl. Acad. Sci.*, vol. 89, 2581–2584.
Richman, C. et al, (1976) *Blood*, vol. 47 No. 6, 1031–1039.
Richmond, A. et al, (1986) *J. Cell Phys.*, vol. 129, 375–384.
Ripka, W. et al, (1993) *Tetrahedron*, vol. 49 No. 17, 3593–3608.
Rosenfeld, M. et al, (1991) *Science*, vol. 252, 431–434.
Rosenfeld, M. et al, (1992) *Cell*, vol. 68, 143–155.
Rudick, R. et al, (1998) *Neurology*, vol. 50 No. 5, 1294–1300.
Sabers, A.. et al, (1995) *Acta. Neurol. Scand.*, vol. 92, 19–27.
Sambrook, J. et al, (1989) *Cold Spring Harbor Laboratory Press*.
Samulski, R. et al, (1989) *J. Virology*, vol. 63 No. 9, 3822–3828.
Schiffer, C. et al, (1983) *Ann. N.Y. Acad. Sci.*, 161–169.
Schultz, L. et al, (1987) *Gene*, vol. 54, 113–123.
Schwarting, A. et al, (1998) *J. Immunol.*, vol. 161, 494–503.
Seed, B., (1987) *Nature*, vol. 329, 840–842.
Shimoda, K. et al, (1993) *J. Clin. Invest.*, vol. 91 No. 4, 1310–1313.
Shirozu, M. et al, (1995) *Genomics*, vol. 28, 495–500.
Siena, S. et al, (1989) *Blood*, vol. 74 No. 6, 1905–1914.
Smith, G. et al, (1983) *Mol. Cell Biol.*, vol. 3 No. 12, 2156–2165.
Stiff, P. et al, (1983) *Transfusion*, vol. 23, 500–503.
Strieter, M. et al, (1989) *Science*, vol. 253, 1467–1469.
Strieter, R. et al, (1989) *J. Biol. Chem.*, vol. 264 No. 18, 10621–10626.
Tashiro, K. et al, (1993) *Science*, vol. 261, 600–603.
Thelen, M. et al, (1988) *FASEB J.* vol. 2, 2702–2706.
To, L. et al, (1992) *Bone Marrow Transplantation* vol. 9, 277–284.
Tokuda, A. et al, (2000) *J. Immunol.*, vol. 164, 2745–2751.
Tratschin, J. et al, (1984) *J. Virology*, vol. 51 No. 3, 611–619.
Tratschin, J. et al, (1984) *Mol. Cell Biol.*, vol. 4 No. 10, 2072–2081.
Tratschin, J. et al, (1985) *Mol. Cell Biol.*, vol. 5 No. 11, 3251–3260.
Tsuji, T. et al, (1990) *Proc. Natl. Acad. Sci.*, vol. 87, 8835–8839.

Unemori, E. et al, (1992) *J. Biol. Chem.*, vol. 268 No. 2, 1338–1342.
van Beuschem, V. et al, (1992) *Proc. Natl. Acad. Sci.*, vol. 89, 7640–7644.
Verfaillie, C. et al, (1990) *J. Exp. Med.*, vol. 172, 509–520.
von Tscharner, V. et al, (1986) *Nature*, vol. 324, 369–372.
Wang, J. et al, (1998) *Blood*, vol. 92 No. 3, 756–764.
Warringa, R. et al, (1991) Blood, vol. 77 No. 12, 2694–2700.
Weber, F. et al, (1998) *Annals Neur.*, vol. 44 No. 1, 27–34.
Wess, G. et al, (1992) *Tetrahedron Letters*, vol. 33 No. 2, 195–198.
Wess, G. et al, (1993) *Tetrahedron Letters*, vol. 34 No. 5, 817–818.
Wilson, J. et al, (1988) *Proc. Natl. Acad. Sci.*, vol. 85, 3014–3018.
Wilson, J. et al, (1992) *J. Biol. Chem.*, vol. 267 No. 2, 963–967.
Wolfe, J. et al, (1990) *Science*, vol. 247, 1465–1468.
Wondisford, F. et al, (1988) *Molecular Endocrinology*, vol. 2 No. 1, 32–39.
Wu.; G. et al, (1988) *J. Biol. Chem.*, vol. 263 No. 29, 14621–14624.
Ying, S. et al, (1999) *J. Immunol.*, vol. 163, 6321–6329.
Yla–Herttuala, S. et al, (1991) *Proc. Natl. Acad. Sci.*, vol. 88, 5252–5256.
Yu, C. et al, (1998) *Immunology*, vol. 95, 480–487.
Zhou, N. et al, (2000) *Biochemistry 2000*, vol. 39, 3782–3787.
Zsebo, K. et al, (1990) *Cell*, vol. 63, 195–201.
Levine, Lawrence, et al., "Analogs of anthracene, phenathrene, and benzoflavone inhibit prostaglandin biosynthesis by cells in culture", *Prostaglandins* (1977), 14(1), 1–9, XP–001077002.
Database WP1, Week 199246, Sep. 20, 1992, Derwent Publications Ltd., London. GB; AN 1992–376280, XP–002199686, Oishi, Takeshi, et al., "Phenanthrene derivative" & JP 04 275247 A (Meiji Seika Kaisha), Sep. 30, 1992 Abstract & Patent Abstracts of Japan, vol. 017, No. 067 (C–1025), Feb. 10, 1993 & JP 04 275247 A (Meiji Seika Kaisha Ltd.), Sep. 30, 1992 (Abstract).
Virag, Laszlo, et al., "Cytoprotective effects of novel phenanthridinone inhibitors of poly(ADP–ribose) polymerase", *Faseb Journal*, (Mar. 7, 2001) vol. 15, No. 4, pp. A567, XP–008003296.
Liaudet, Lucas et al., "Activation of poly(ADP–ribose) polymerase–1 is a central mechanism of lipopolysaccharide–induced acute lung inflammation", *American Journal of Respiratory and Critical Care Medicine*, vol. 165, No. 3, Feb. 1, 2002, pp. 372–377, XP–008003289.
Mabley, J., G., et al., "Anti–inflammatory effects of a novel, potent inhibitor of poly(ADP–ribose) polymerase", *Inflammation Research* (2001), 50(11), 561–569, XP–001076853.

* cited by examiner

Figure 2
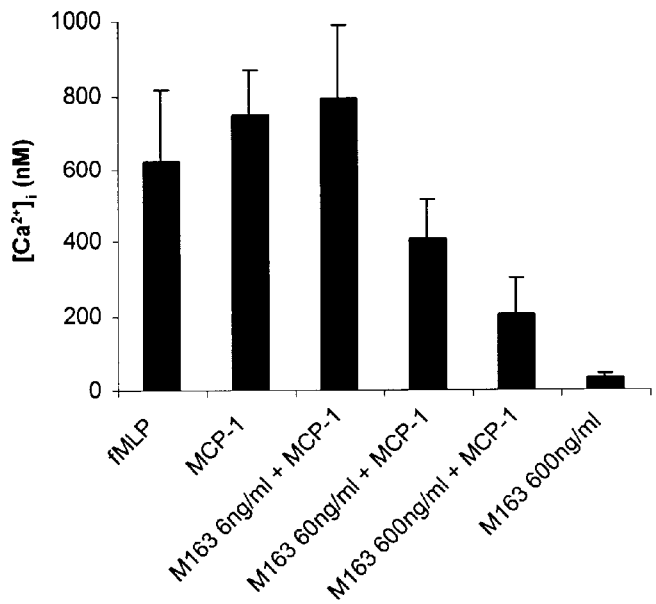
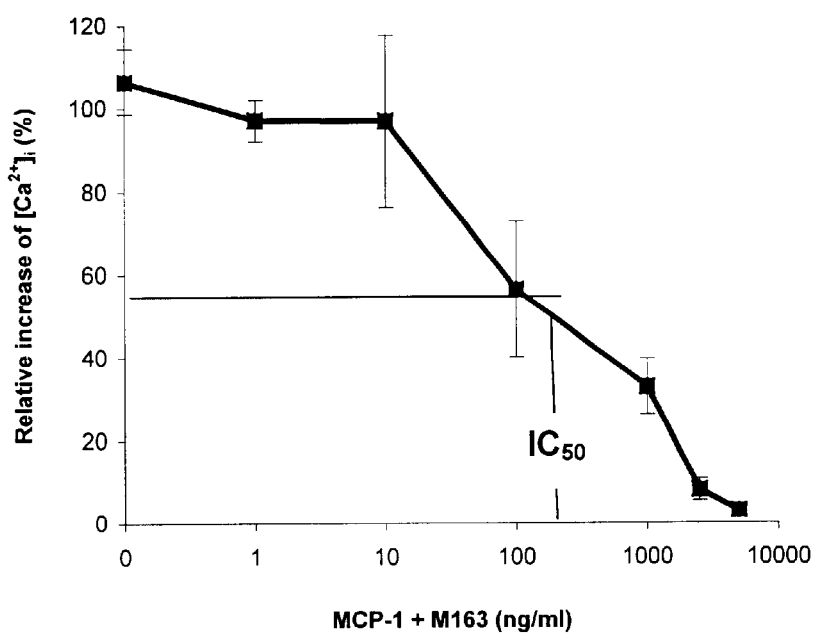
A. Absolute $[Ca^{2+}]_i$ mobilization in response to given conditions.
B. Relative effect of increasing concentration of phenanthrene-9,10-dione on MCP-1 associated induction of $[Ca^{2+}]_i$ mobilization Determination of the effect of CTCM163 on TNF-α induced caspase-3 activity in human neutrophils by fluorometric analysis.

Increasing concentration of Phenanthrene-9,10-dione

A = IL-8 (10nM)
B = IL-8 + Phenanthrene-9,10-dione (0.03 µM)
C = IL-8 + Phenanthrene-9,10-dione (0.3 µM)
D = IL-8 + Phenanthrene-9,10-dione (3.0 µM)
E = IL-8 + Phenanthrene-9,10-dione (30 µM)

THERAPEUTICS FOR CHEMOKINE MEDIATED DISEASES

FIELD OF THE INVENTION

The invention relates to small molecule therapeutics, particularly tricyclic compounds such as phenanthrene diones.

BACKGROUND OF THE INVENTION

Chemokines are chemotactic cytokines that belongs to a large family of chemoattractant molecules involved in the directed migration of immune cells (Schall, T. The Chemokines. *In The Chemokine Handbook*; Thompson, A., Ed., Academic Press: San Diego, Calif., 1994; pp419–460). The physiological role of chemokines in the immune process is to elicit mobilization of immune cells against pathogenic organisms by direct recruitment and activation.

Chemokines are small proteins that are divided into two main classes, based on the position of the first two cysteines, the C—X—C and C—C families of chemokines (two smaller branches of this family have been described, the C and $CX_3C$ subfamilies). Chemokines and their receptors have been implicated as having important roles in a number of disease states, including Guillian-Barre Syndrome (GBS), Rheumatoid arthritis (RA), Allograft rejection, Psoriasis, Atherosclerosis, Asthma, Angiogenesis, Inflammatory Bowel Disease (IBD), Acute Respiratory Distress Syndrome (ARDS), and all other diseases known as autoimmune diseases.

In addition to their well-established role in the immune systems, recent studies strongly suggesting their involvement in the maintenance of Central Nervous System (CNS) homeostasis, in neuronal patterning during ontogeny and as potential mediators of neuroinflammation, playing an essential role in leukocyte infiltration into the brain (Mennicken, F. et. al., (1999) *Trends Pharmacol. Sci.* 20 (2): 73–78). Their expression is rapidly induced by various neuroinflammatory stimuli, implicating them in various neurological disorders such as trauma, stroke, and Amyotropic Lateral Sclerosis (ALS), Parkinson's, and Alzheimer's disease, in tumor induction and in neuroimmune disease such as multiple sclerosis (MS) or acquired immunodeficiency syndrome (AIDS). Both MS and GBS, are initiated by an autoimmune reaction involving T-lymphocytes (T-cells).

Multiple Sclerosis (MS) is a disease that primarily afflicts young adults. The diseases is often initially characterized by temporary partial paralysis, with remission of disease followed by relapses of greater severity and duration resulting ultimately in permanent disability in many cases. One of the hallmarks of MS disease is the infiltration and activation of peripheral blood leukocytes into the brain. This along with central nervous system immune cell activation may lead to active demyelination of the central nervous system.

Psoriasis, a common genetic skin disease, is a well known angiogenesis-dependent disorder that is characterized by marked dermal neovascularization. Keratinocytes isolated from psoriatic plaques demonstrate a greater production of angiogenic activity, as compared to normal keratinocytes. This aberrant phenotype is due, in part, to a combined defect in the overproduction of the angiogenic cytokine IL-8, and a deficiency in the production of the angiogenesis inhibitor, thrombospondin-1, resulting in a proangiogenic environment (Keane, M. P. and Strieter, R. M. (1999) in Mantovani A (ed): *Chemokines*. Chem Immunol. Basel, Karger, 72: 86–101).

In rheumatoid arthritis (RA), the unrestrained proliferation of fibroblasts and capillary blood vessels leads to the formation of prolonged and persistent granulation tissue of the pannus whose degradative enzymes contribute to profound destruction of joint spaces. In both psoriasis and rheumatoid arthritis, CXC Chemokine specifically IL-8 plays a very important role (Nickoloff, B. J. et. al., (1994) *Am. J. Pathol.* 144: 820–828). Finding an antagonist for these specific chemokines or Chemokine receptors can be a novel approach in the treatment of solid tumors, inflammatory diseases and chronic fibroproliferative disorders.

Atherosclerosis is a disease appearing not only at old age but also in early adulthood. Atherosclerosis is a cardiovascular disease related to the accumulation of fatty streak around arteries. These arterial fatty streaks are composed of lipid-laden macrophages (foam cells) and is the precursor of more complex and dangerous lesions. The participation of inflammatory cells in atherosclerosis is a well known process that involves numerous molecules including chemotactic cytokines (chemokines) for their entry into the vessel wall. The CC Chemokine, MCP-1 and its receptor, CCR-2, has been identified as an extremely potent and has been cloned and characterized in some detail (Charo, I. F. (1999) Mantovani A (ed): *Chemokines*, Chem Immunol. Basel, Karger, 72: 30–41). With regard to CCR, the available studies support an important role for MCP-1 in the development of early atherosclerosis lesions and in T-cell polarizations. The role of classic CXC Chemokine, IL-8 (KC/growth-related oncogene alpha in mice) and its receptor CXCR-2 has shown physiological significance in pathogenesis of atherosclerosis. CXCR-2 is strongly expressed on macrophages (Mphi) in atherosclerosis lesion (Boisvert, W. A. et. al., (2000) *Immunol. Res.* 21(2–3): 129–137).

During inflammation, neutrophils are removed from inflammatory sites by a process of programmed cell death known as apoptosis, leading to their recognition and phagocytosis by macrophages (Savill, J. S. et. al., (1989) *Journal of Clinical Investigation* 83:865). Any significant delay in neutrophil apoptosis can lead to excessive accumulation and damage to surrounding tissues (Hallet, M. B. and Lloyds, D., (1995) *Immunology Today* 16: 264). Tumor necrosis factor-alpha (TNF-α) has been shown to induce extensive apoptosis in neutrophils within three hours.

This is the latest field in research to understand the cause of acute inflammatory diseases such as, inflammatory bowel diseases (IBD) and acute respiratory distress syndrome (ARDS). Finding an inhibitor which can inhance apoptosis can lead to disease cure for rheumatoid arthritis, inflammatory bowl disease, lung disease, gouty inflammation, and ARDS etc. Activated neutrophils plays a major role in the pathogenesis of acute respiratory distress syndrome, and persistence of pulmonary neutrophils is related to poor survival. Granulocyte colony stimulating factor (G-CSF) as well as IL-8 plays a role in the mechanisms of pulmonary neutrophilia in acute respiratory distress syndrome (Aggarwal, A. et. al., (2000) *Eur. Respir. J.* 15(5): 895–901 and Dunican, A. L. et. al., (2000) *Shock* 14(3):248–288, discussion page 288–289) as well as in inflammatory bowl diseases (Brannigan, A. E. et. al., (2000) *Shock* 13(5): 361–366).

Monocyte chemoattractant protein-1 (MCP-1) was the first CC Chemokine to be characterized biologically and has been shown to attract monocytes but not neutrophils (Baggiolini M, Dewald B, Moser B. (1994) Interleukin-8 and related chemotactic cytokines —CXC and CC chemokines. *Adv. Immunol.* 55:97–179). MCP-1 is a member of the β-Chemokine family which acts through specific receptors to recruit monocytes, basophils, and T-lymphocytes to sites of inflammation.

MCP-1 has been reported to stimulate an increase in cytosolic free calcium and the respiratory burst in monocytes, and to activate monocyte-mediated tumoristatic activity, as well as to induce tumoricidal activity (see for example Rollins, *Mol. and Cell. Biol.* 11:3125–31(1991) and Walter, (1991) *Int. J. Cancer* 49:431–35. MCP-1 has been implicated in mediating monocytic infiltration of tissues in inflammatory processes such as rheumatoid arthritis and alveolitis (see for example Koch, (1992) *J. Clin. Invest.* 90:772–79 and Jones, (1992) *J. Immunol.* 149:2147–54). Existing data suggest that MCP-1 may play an important role in the recruitment of monocyte-macrophages to atherosclerotic lesions (see for example, Nelken, (1991) *J. Clin. Invest* 88:1121–27, Yla-Herttuala, (1991) *Proc. Nat'l. Acad. Sci.* USA 88:5252–56 and Cushing, (1990) *Proc. Natl. Acad. Sci.* USA 87:5134–38). In animal models, MCP-1 has been shown to be expressed in the brain after focal ischemia (Kim, J. S., (1995) *J. Neuroimmunol.* 56, 127–34; Wang, X., et al. (1995) *Stroke* 26, 661–5), and during experimental autoimmune encephalomyelitis (Hulkower, K., et al. (1993) *J. Immunol.* 150, 2525–33; Ransohoff, R. M., et al. (1993) 7, 592–600). MCP-1 is therefore implicated as an important mediator of the disease process for which these systems serve as animal models, such as atherosclerosis and multiple sclerosis.

In psoriatic lesions, it has been suggested that MCP-1 regulates the interaction between proliferating keratinocytes and dermal macrophages, and that MCP-1 may also serve to recruit mononuclear cells (Schroder, J. M. (1992) *Arch. Dermatol. Res* 284 Suppl 1, S22–6; Gillitzer, R., et al (1993) *J. Invest. Dermatol.* 101, 127–31). It has recently been shown that MCP-1 acts on CD4+ and CD8+ T lymphocytes as a chemoattractant both in vitro and in vivo, in addition to its effect on monocytes (Loetscher, P., et al. (1994) *FASEB J.* 8, 1055–60; Carr, M. W., et al. (1994) *Proc. Natl. Acad. Sci.* USA 91, 3652–6; Taub, D. D., et al. (1995) *J Clin Invest.* 95(3):1370–6). Natural killer cells that have been stimulated by interleukin-2, are also subject to chemotaxis by MCP-1 (Maghazachi, A A., et al. (1994) *J. Immunol.* 153, 4969–77; Allaven, P., et al. (1994) *Eur. J. Immunol.* 24, 3233–6. The existing data therefore indicates that MCP-1 plays a role in the recruitment of effector cells into a wide range of inflammatory lesions.

In addition to the effects on monocytes and T lymphocytes, MCP-1 has been shown to be a moderate chemoattractant and potent activator of allergy mediator release, such as histamine and leukotrienes, from basophils (Kuna, P., et al. (1992) *J. Exp. Med.* 175, 489–93; Bischoff, S. C., et al. (1992) *J. Exp. Med.* 175, 1271–7; Bischoff, S. C., et al. (1993) *Eur. J. Immunol.* 23, 761–7).

The MCP-1 receptor is reportedly expressed in two forms that differ because of alternative splicing of the mRNA in the region encoding the carboxy-terminal of the protein. The alternative forms have been designated MCP-1-RA and MCP-1-RB (Charo, I. F., et al. (1994) *Proc. Natl. Acad. Sci.* USA, 91, 2752–56). These receptors are together designated herein as CCR-2, and appear to be expressed in monocytes, myeloid precursor cells and activated T lymphocytes (Myers, S. J., et al, 1995. *J. Biol. Chem.*, 270, 5786–5792, Qin, S. et al. 1996. *Eur. J. Immunol.* 26, 640–647). CCR-2 has been cloned (see U.S. Pat. No. 6,132,987 issued to Charo et al. Oct. 17, 2000), disclosing a sequence that indicates that CCR-2 belongs to a family of seven transmembrane-type chemokine receptors.

U.S. Pat. No. 6,084,075 issued to Lind et al. on Jul. 4, 2000 discloses agonist and antagonist antibodies to CCR-2, and teaches that such antibodies may be useful for treating diseases such as inflammation, rheumatoid arthritis, mononuclear-phagocyte dependent lung injury, idiopathic pulmonary fibrosis, sarcoidosis, focal ischemia, autoimmune encephalomyelitis, stroke, multiple sclerosis, psoriatic lesions, and chronic transplant rejection.

Interleukin-8 (IL-8) belongs to the CXC chemokine family. Many different names have been applied to IL-8, such as neutrophil attractant/activation protein-one (NAP-1), monocyte derived neutrophil chemotactic factor (MDNCF), neutrophil activating factor (NAF), and T-cell lymphocyte chemotactic factor. IL-8 is a chemoattractant for neutrophils, basophils, and a subset of T-cells. It is produced by a majority of nucleated cells including macrophages, fibroblasts, endothelial and epithelial cells exposed to TNF, IL-1α, IL-1β or LPS, and by neutrophils themselves when exposed to LPS or chemotactic factors such as fMLP (Baggiolini M., et. al., (1989) *Journal of Clinical Investigation* 84: 1045; Schroder, J. et. al., (1987) *Journal of Immunology* 139: 3474; ibid, (1990) *Journal of Immunololgy* 144: 2223; Strieter et. al., (1989) *Science* 243: 1467; ibid, (1989) *Journal of Biological Chemistry* 264: 10621; Cassatella et. al., (1992) *Journal of Immunology* 148: 3216).

Two receptors for IL-8, CXCR-1 (IL-8RA/R1) and CXCR-2 (IL-8RB/R2), are expressed on neutrophils (Baggiolini, M. et. al., (1997) *Annual Review of Immunology* 15: 675–705). They share 77% identical amino acids, and their genes are colocalized on chromosome 2q35 (Holmes, W. E. et. al., (1991) *Science* 253:1278–1280 and Murphy, P. M. and Tiffany, H. L., (1991) *Science* 253: 1280–1283). One receptor, CXCR-2, has high affinity for IL-8 and all other CXC chemokines that attract neutrophils (e.g. the GRO proteins, NAP-2, etc.), while the other, CXCR-1, has high affinity for IL-8 only (Baggiolini, M. et. al., (1994) *Adv. Immunol.* 55: 97–179). IL-8 receptors are also found on monocytes, basophils, and eosinophils, but the responses of these cells to IL-8 are much weaker than those of neutrophils (Baggiolini, M. et. al., (1994) *Adv. Immunol.* 55: 97–179).

IL-8 exerts its biological activities by binding to specific cell surface receptors, CXCR-1, and CXCR-2. Both receptors binds IL-8 with high affinity but they have different affinities for MGSA/Groalpha and NAP-2. It has been shown that the expression of epidermal CXCR-2 is increased in psoriasis, suggesting that activation of keratinocytes (KC) mediated by CXCR-2 contributes to the characteristic epidermal changes observed in psoriasis (Kondo, S. et. al., (2000) *J. Cell Physiol.* 183(3): 366–370).

IL-8 (ELR+) was the first CXC Chemokine to be found to induce angiogenesis (Keane, M. P. and Strieter, R. M., The Role of CXC Chemokines in the Regulation of Angiogenesis, Mantovani, A. (ed.): (1999) *Chemokines*, Chem. Immunol. Basel, Karger 27: 86–101). IL-8 was shown to mediate both in-vitro endothelial cell chemotactic and proliferative activity, as well as in-vivo angiogenesis in the absence of preceding inflammation using bioassays of angiogenesis (Strieter, R. M. et. al., (1992) *American Journal of Pathology* 141: 1279–1284). In continuation to this, IL-8 been found to be significantly elevated in non-small cell lung cancer (NSCLC) (Smith, D. R. et. al., (1994) *Journal of Experimental Medicine* 179: 1409–1415). In Addition, IL-8 was determined to be a major angiogenic factor contributing to overall tumor-derived angiogenic activity in NSCLC (Arenberg, D. A. et. al., (1995) *Journal of Investigation Medicine* 43: (suppl 3) 479A).

SUMMARY OF THE INVENTION

In various aspects, the invention provides methods for the use of chemokine-receptor-binding compounds (which may be chemokine receptor ligands such as chemokine receptor agonists or antagonists), or salts thereof, in treating chemokine or chemokine receptor mediated diseases, such as MCP-1 or IL-8 mediated diseases, or diseases mediated by chemokine receptors CXCR-1, CXCR-2, CCR-2 and CCR-4.

In some embodiments, the invention relates to methods of using a tricyclic compound of formula (I), (II), (III) or (IV), or a pharmaceutically acceptable salt thereof, to formulate a medicament for the treatment of a chemokine mediated disease state, or to treat such a disease:

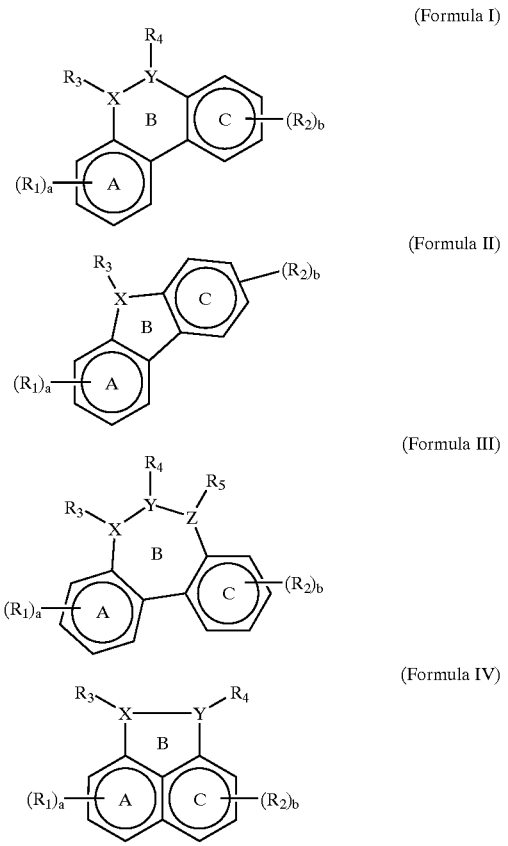

(Formula I)

(Formula II)

(Formula III)

(Formula IV)

In the foregoing formulae: "a" may be 0 or an integer from 1 to 4 (with a maximum of 3 in the case of formula IV); "b" may be 0 or an integer from 1 to 4 (with a maximum of 3 in the case of formula IV); "X" may be C or N; "Y" may be C or N; and, "Z" may be C or N. Where "a" or "b" are greater than 1, the relevant substituents need not be the same, so that if a=2 in the substituent $(R_1)_2$, the two $R_1$ groups may be the same or different.

In some embodiments, ring A may be aromatic and may be heterocyclic with one or more heteroatoms selected from the group consisting of oxygen and nitrogen. Ring C may be aromatic and may be heterocyclic with one or more heteroatoms selected from the group consisting of oxygen and nitrogen. Ring B may be aromatic or non-aromatic and may be heterocyclic with one or more heteroatoms selected from the group consisting of oxygen and nitrogen.

In alternative embodiments, $R_1$ and $R_2$ at each occurance may independently be selected from substituents having a selected number of atoms, such as 100, 50, 25, 20, 15, 10, 5 or fewer atoms, wherein the substituent may be selected from the group consisting of: H; substituted or unsubstitued alkyls, such as, $C_{1-10}$ alkyls, $C_{1-6}$ alkyls; substituted or unsubstitued cycloalkyls, such as $C_{3-6}$ cycloalkyls; substituted or unsubstitued alkenyls, such as $C_{2-6}$ alkenyls; substituted or unsubstitued alkynyls, such as $C_{2-6}$ alkynyls; substituted or unsubstitued aryls; substituted or unsubstitued heterocycles; hydroxyls; aminos; nitros; thiols; primary, secondary or tertiary amines; imines; amides; phosphonates; phosphines; carbonyls; carboxyls; silyls; ethers; thioethers; sulfonyls; sulfonates; selenoethers; ketones; aldehydes; esters; —$CF_3$; —CN; and combinations thereof.

In alternative embodiments, $R_3$, $R_4$ and $R_5$ at each occurance may independently be selected from substituents having a selected number of atoms, such as 100, 50, 25, 20, 15, 10, 5 or fewer atoms, wherein the substituent may be selected from the group consisting of: H; substituted or unsubstitued alkyls, such as $C_{1-5}$ alkyls; substituted or unsubstitued cycloalkyls, such as $C_{3-5}$ cycloalkyls; substituted or unsubstitued alkenyls, such as $C_{2-5}$ alkenyls; substituted or unsubstitued alkynyls, such as $C_{2-6}$ alkynyls; substituted or unsubstitued aryls; substituted or unsubstitued heterocycles; hydroxyls; aminos; nitros; thiols; primary, secondary or tertiary amines; imines; amides; phosphonates; phosphines; carbonyls; carboxyls; silyls; ethers; thioethers; sulfonyls; sulfonates; selenoethers; ketones; aldehydes; esters; —$CF_3$; —CN; and combinations thereof.

In some embodiments, there may be at least one hydrogen bond acceptor at or attached to position X, Y, R3, R4 or R5, which may for example be attached directly to such a position (i.e. attached at the selected position by one chemical bond with no intervening atoms).

In some embodiments, the chemokine may be selected from the group consisting of: IL-8, MCP-1, and chemokines that bind to a chemokine receptor in a mammal selected from the group such as CXCR-1, CXCR-2, CCR-2 and CCR-4.

In various embodiments, the invention provides for the use of compounds of the invention in the treatment of diseases selected from the group consisting of inflammation, acute inflammation, chronic inflammation, atherosclerosis, psoriasis, gout, acute pseudogout, acute gouty arthritis, arthritis, rheumatoid arthritis, allograft rejection, chronic transplant rejection, asthma, stroke, mononuclear-phagocyte dependent lung injury, idiopathic pulmonary fibrosis, sarcoidosis, focal ischemia, autoimmune encephalomyelitis, multiple sclerosis, atopic dermatitis, asthma, chronic obstructive pulmonary disease, adult respiratory distress syndrome, inflammatory bowel disease. Crohn's disease, ulcerative colitis, septic shock, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, and angiogenesis.

Methods of the invention may comprise administering an effective amount of a tricyclic compound of the invention, such as phenanthrene-9,10-dione, or a pharmaceutically acceptable salt thereof, to a patient in need of such treatment. The invention also provides pharmaceutical compositions for use in such therapy, optionally comprising a pharmaceutically acceptable excipient, diluent or carrier.

In another aspect, the invention provides methods of inhibiting the binding of a chemokine, such as MCP-1 or IL-8, to its receptors, such as CXCR-1, CXCR-2, CCR-2 and CCR-4. Such methods may be used in vivo, such as in a mammal, or in vitro. Such methods may comprise administering to a mammal an effective amount of a compound of the invention, such as phenanthrene-9,10-dione.

BRIEF DESCRIPTION OF THE DRAWINGS

FIG. 2 shows inhibition effect of phenanthrene-9,10-dione on MCP-1 induced $[Ca^{+2}]_i$ mobilization.

DETAILED DESCRIPTION OF THE INVENTION

Figure 1:
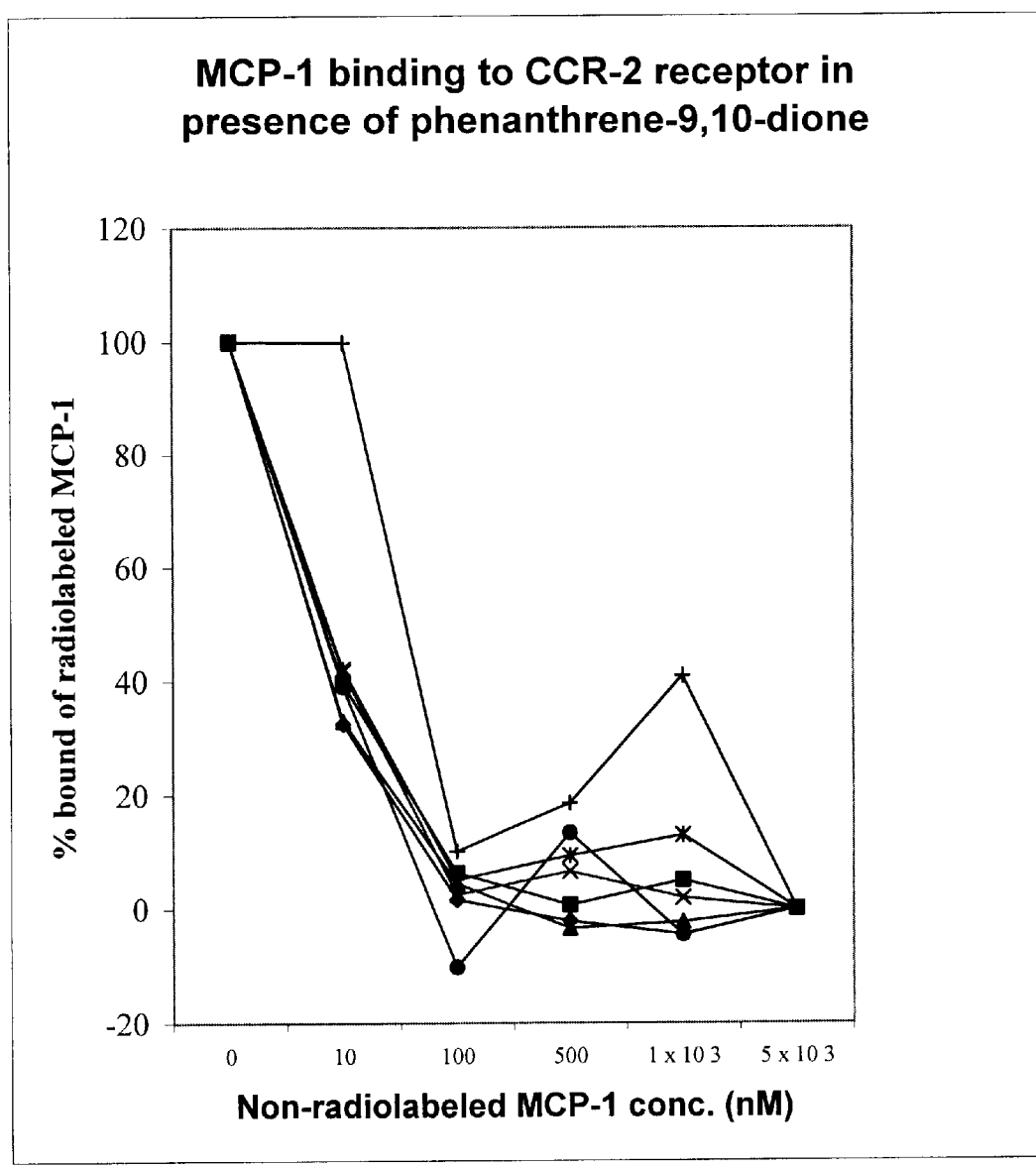
FIG. 1 shows the inhibitory effect of phenanthrene-9,10-dione on the binding of MCP-1 to CCR-2. A dose response of phenanthrene-9,10-dione at different concentration in comparison to MCP-1.

In some embodiments, the compounds of the invention comprise moieties involved in hydrogen bonding, as hydrogen bond acceptors. As is generally understood in the art, a hydrogen bond comprises one or more hydrogen bond acceptor atoms and one or more hydrogen bond donor atoms. A hydrogen bond acceptor is an atom in an appropriate molecular environment, which generally renders the atom sufficiently electronegative, and which has an unshared electron pair which is thereby able to interact with a hydrogen atom that is covalently attached to the hydrogen bond donor. Hydrogen bond acceptors of the present invention may for example include O, N or S atoms. Some substituent groups such as hydroxyls or primary or secondary amines can act as both hydrogen bond donors and hydrogen bond acceptors. Groups such as carbonyls, ethers or tertiary amines are hydrogen bond acceptors only. Hydrogen bond acceptors of the present invention may be in substituents such as carbonyls (C=O) and their thio derivatives (C=S), primary, secondary, and tertiary amines, hydroxyls, ethers, amides, esters, fluoro, chloro and bromo groups and thiols and thioethers.

In some embodiments, the compounds of the invention may have a chemokine receptor binding affinity ($IC_{50}$) below 1000 nM, below 100 nM, below 50 nM, below 10 nM or below 1 nM; and may have a selective affinity for a selected chemokine receptor, such as a 10-fold selective affinity, a 50-fold selective affinity or a 100-fold selective affinity, for a selected chemokine receptor relative to an alternative chemokine receptor. For example, in some embodiments, the compounds may have a binding affinity for CCR-2 of below 100 nM, below 50 nM, below 10 nM or below 1 nM. Receptor binding affinities may by assayed by any of a number of standard methods, such as competitive displacement of radioactively labeled ligands.

In various aspects, the invention relates to compounds having alternative substitutions and substituent groups, designated in formulae herein as "R", typically with a numeric subscript to identify the substituent group. A substituent group is generally a group that replaces one or more hydrogen atoms attached to a parent structure. Where there are a variable number of substituent groups in a structural formula, the selected number will reflect the limitations of the parent structure, so that in a formula that provides for 0–4 substituents, where the selected parent structure has space for only 3 substituents, one skilled in the art will select 0–3 substituents. The organic substituent groups are for example identified in the Handbook of Chemistry and Physics, 79th Edition, CRC Press (all of which are hereby incorporated by reference). Substituent groups of the invention may for example be selected from groups having from 1 to 100 atoms, such as groups having 100 or fewer, 50 or fewer, 25 or fewer, 20 or fewer, 15 or fewer, 10 or fewer, 5 or fewer, 4, 3, 2, or 1 atom(s). Atoms in such substituents may for example be selected from the group consisting of carbon, hydrogen, oxygen, nitrogen, halogen, sulfur, silicon, arsenic, boron, selenium and phosphorus.

Substituent groups may for example be substituted or unsubstitued alkyls, such as, $C_{1-10}$ alkyls, $C_{1-6}$ alkyls; substituted or unsubstitued cycloalkyls, such as $C_{1-10}$ cycloalkyls, $C_{3-6}$ cycloalkyls; substituted or unsubstituted alkenyls, such as $C_{1-10}$ alkenyls, $C_{2-6}$ alkenyls; substituted or unsubstituted alkynyls, such as $C_{1-10}$ alkynyls, $C_{2-6}$ alkynyls; substituted or unsubstitued aryls; substituted or unsubstitued heterocycles; hydroxyls; aminos; nitros; thiols; primary, secondary or tertiary amines; imines; amides; phosphonates; phosphines; carbonyls; carboxyls; silyls; ethers; thioethers; sulfonyls; sulfonates; selenoethers; ketones; aldehydes; esters; —$CF_3$; —CN; and combinations thereof. Substituent groups which are themselves substitued may be substitued with the similar substituents.

In some embodiments, a substituent group may comprise a cyclic, heterocyclic or polycyclic group. The term "cyclic group", as used herein, includes cyclic saturated or unsaturated (optionally aromatic) group having from 3 to 10, 4 to 8, or 5 to 7 carbon atoms. Exemplary cyclic groups include cyclopropyl, cyclobutyl, cyclopentyl, cyclohexyl, and cyclooctyl. Cyclic groups may be unsubstituted or substituted at one or more ring positions. A cyclic group may for example be substituted with halogens, alkyls, cycloalkyls, alkenyls, alkynyls, aryls, heterocycles, hydroxyls, aminos, nitros, thiols, amines, imines, amides, phosphonates, phosphines, carbonyls, carboxyls, silyls, ethers, thioethers, sulfonyls, sulfonates, selenoethers, ketones, aldehydes, esters, —$CF_3$, —CN.

The term "heterocyclic group" includes cyclic saturated, unsaturated and aromatic groups having from 3 to 10, 4 to 8, or 5 to 7 carbon atoms, wherein the ring structure includes about one or more heteroatoms. Heterocyclic groups may include pyrrolidine, oxolane, thiolane, imidazole, oxazole, piperidine, piperazine, morpholine. The heterocyclic ring may be substituted at one or more positions with such substituents as, for example, halogens, alkyls, cycloalkyls, alkenyls, alkynyls, aryls, other heterocycles, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —CF$_3$, —CN. Heterocycles may also be bridged or fused to other cyclic groups as described below.

The term "polycyclic group" as used herein is intended to refer to two or more saturated, unsaturated or aromatic cyclic rings in which two or more carbons are common to two adjoining rings, so that the rings are "fused rings". Rings that are joined through non-adjacent atoms may be termed "bridged" rings. Each of the rings of the polycyclic group may be substituted with such substituents as described above, as for example, halogens, alkyls, cycloalkyls, alkenyls, alkynyls, hydroxyl, amino, nitro, thiol, amines, imines, amides, phosphonates, phosphines, carbonyls, carboxyls, silyls, ethers, thioethers, sulfonyls, selenoethers, ketones, aldehydes, esters, —CF$_3$, or —CN.

The term "alkyl" refers to the radical of saturated aliphatic groups, including straight chain alkyl groups, branched-chain alkyl groups, cycloalkyl (alicyclic) groups, alkyl substituted cycloalkyl groups, and cycloalkyl substituted alkyl groups. In some embodiments, a straight chain or branched chain alkyl has 20 or fewer carbon atoms in its backbone ($C_1$–$C_{20}$ for straight chain, $C_3$–$C_{20}$ for branched chain), or 10 or fewer carbon atoms. In some embodiments, cycloalkyls may have from 4–10 carbon atoms in their ring structure, such as 5, 6 or 7 carbon rings. Unless the number of carbons is otherwise specified, "lower alkyl" as used herein means an alkyl group, as defined above, having from one to ten carbon atoms in its backbone structure. Likewise, "lower alkenyl" and "lower alkynyl" have chain lengths of ten or less carbons.

The term "alkyl" (or "lower alkyl") as used throughout the specification and claims is intended to include both "unsubstituted alkyls" and "substituted alkyls", the latter of which refers to alkyl moieties having substituents replacing a hydrogen on one or more carbons of the hydrocarbon backbone. Such substituents can include, for example, halogen, hydroxyl, carbonyl (such as carboxyl, ketones (including alkylcarbonyl and arylcarbonyl groups), and esters (including alkyloxycarbonyl and aryloxycarbonyl groups)), thiocarbonyl, acyloxy, alkoxyl, phosphoryl, phosphonate, phosphinate, amino, acylamino, amido, amidine, imino, cyano, nitro, azido, sulfhydryl, alkylthio, sulfate, sulfonate, sulfamoyl, sulfonamido, heterocyclyl, aralkyl, or an aromatic or heteroaromatic moiety. The moieties substituted on the hydrocarbon chain can themselves be substituted, if appropriate. For instance, the substituents of a substituted alkyl may include substituted and unsubstituted forms of aminos, azidos, iminos, amidos, phosphoryls (including phosphonates and phosphinates), sulfonyls (including sulfates, sulfonamidos, sulfamoyls and sulfonates), and silyl groups, as well as ethers, alkylthios, carbonyls (including ketones, aldehydes, carboxylates, and esters), —CF$_3$, —CN and the like. Exemplary substituted alkyls are described below. Cycloalkyls can be further substituted with alkyls, alkenyls, alkoxys, alkylthios, aminoalkyls, carbonyl-substituted alkyls, —CF$_3$, —CN, and the like.

The terms "alkenyl" and "alkynyl" refer to unsaturated aliphatic groups analogous in length and possible substitution to the alkyls described above, but that contain at least one double or triple bond respectively.

The term "aralkyl", as used herein, refers to an alkyl or alkylenyl group substituted with at least one aryl group.

Exemplary aralkyls include benzyl (i.e., phenylmethyl), 2-naphthylethyl, 2-(2-pyridyl)propyl, 5-dibenzosuberyl, and the like.

The term "alkylcarbonyl", as used herein, refers to —C(O)-alkyl. Similarly, the term "arylcarbonyl" refers to —C(O)-aryl. The term "alkyloxycarbonyl", as used herein, refers to the group —C(O)—O-alkyl, and the term "aryloxycarbonyl" refers to —C(O)—O-aryl. The term "acyloxy" refers to —O—C(O)—R$_7$, in which R$_7$ is alkyl, alkenyl, alkynyl, aryl, aralkyl or heterocyclyl.

The term "amino", as used herein, refers to —N(R$_\alpha$)(R$_\beta$), in which R$_\alpha$ and R$_\beta$ are each independently hydrogen, alkyl, alkyenyl, alkynyl, aralkyl, aryl, or in which R$_\alpha$ and R$_\beta$ together with the nitrogen atom to which they are attached form a ring having 4–8 atoms. Thus, the term "amino", as used herein, includes unsubstituted, monosubstituted (e.g., monoalkylamino or monoarylamino), and disubstituted (e.g., dialkylamino or alkylarylamino) amino groups. The term "amido" refers to —C(O)—N(R$_8$)(R$_9$), in which R$_8$ and R$_9$ are as defined above. The term "acylamino" refers to —N(R'$_8$)C(O)—R$_7$, in which R$_7$ is as defined above and R'$_8$ is alkyl.

As used herein, the term "nitro" means —NO$_2$; the term "halogen" designates —F, —Cl, —Br or —I; the term "sulfhydryl" means —SH; and the term "hydroxyl" means —OH.

The term "aryl" as used herein includes 5-, 6- and 7-membered aromatic groups that may include from zero to four heteroatoms in the ring, for example, phenyl, pyrrolyl, furyl, thiophenyl, imidazolyl, oxazole, thiazolyl, triazolyl, pyrazolyl, pyridyl, pyrazinyl, pyridazinyl and pyrimidinyl, and the like. Those aryl groups having heteroatoms in the ring structure may also be referred to as "aryl heterocycles" or "heteroaromatics". The aromatic ring can be substituted at one or more ring positions with such substituents as described above, as for example, halogen, azide, alkyl, aralkyl, alkenyl, alkynyl, cycloalkyl, hydroxyl, amino, nitro, sulfhydryl, imino, amido, phosphonate, phosphinate, carbonyl, carboxyl, silyl, ether, alkylthio, sulfonyl, sulfonamido, ketone, aldehyde, ester, a heterocyclyl, an aromatic or heteroaromatic moiety, —CF$_3$, —CN, or the like. Aryl groups can also be part of a polycyclic group. For example, aryl groups include fused aromatic moieties such as naphthyl, anthracenyl, quinolyl, indolyl, and the like.

Figure 12:
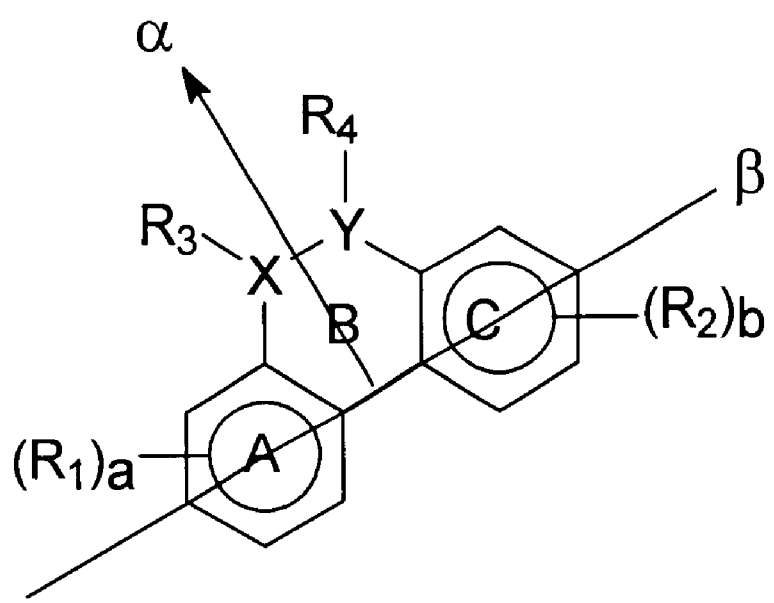
FIG. 12 is a drawing illustrating a structure of some of the compounds of the invention, illustrating the orientation of pharmacophores.

With reference to FIG. 12, in one aspect, the compounds of the invention may comprise two hydrophobic aromatic rings, A and C, linked by a bridge, shown as ring B in FIG. 12. The bridge may comprise one or more hydrogen bond acceptors, and the bridge may be an aromatic or non-aromatic ring. In some embodiments, substitutions may be made to the hydrophobic aromatic rings that preserve the hydrophobic and aromatic characteristic of the rings, such as the substitution of heteroatoms within the ring or exocyclic substituents. Similarly, substitutions may be made in the bridging moiety. In some embodiments, the centers of the hydrophobic rings may be between about 5 Angstroms and about 2 Angstroms apart, as measured along an axis between the rings (shown as line beta in FIG. 12). The hydrophobic rings may be oriented so that they generally lie in the same plane, for example within 0–15 degrees, 1 degree or less, 5 degrees or less, 10 degrees or less, 15 degrees or less, or 20 degrees or less of being coplanar. The hydrogen bond acceptor or acceptors on the bridge may also be capable of orientation generally on the same plane as the hydrophobic rings, with for example the same range of deviation from co-planarity as recited for the hydrophobic rings. The heteroatom of the hydrogen bond acceptor may be positioned so that it is offset from the axis (beta in FIG. 12) which connects the centers of the hydrophobic rings, for example by being offset from that axis by between about 6 Angstroms and about 2 Angstroms (the direction of this offset is shown by line alpha in FIG. 12). The hydrogen bond acceptor may for example be a carbonyl or other dipolar moiety, and the axis of the carbonyl bond or other dipole may be such that oxygen or other heteroatom of the hydrogen bond acceptor may be oriented away from the axis between the hydrophobic rings, with the dipole directed away from the axis between the hydrophobic rings (as shown by the arrow on line alpha of FIG. 12). The carbonyl or other dipolar bond of the hydrogen bond acceptor may for example be orientable to lie at an angle of from 45 degrees to 90 degrees to the axis between the hydrophobic rings (shown as the angle between lines alpha and beta in FIG. 12).

In one aspect, the present invention relates to uses of phenanthrene-9,10-dione (also known as 9,10-phenanthrenequinone or 9,10-phenanthrenedione, CAS Registry No. 84-11-7):

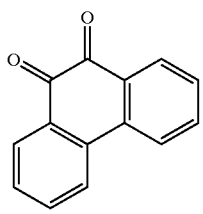

phenanthrene-9,10-dione

In alternative aspects, the compounds of the invention may be selected from the group consisting of compounds having the following formulae:

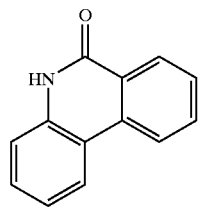

6(5H)phenanthridinone

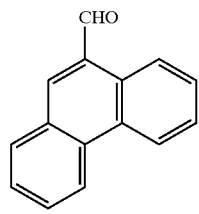

phenanthrene-9-carboxaldehyde

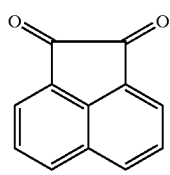

acenaphthenequinone

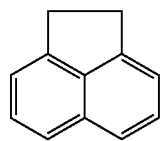

acenaphthene

EXAMPLES

The following examples are illustrative of various aspects of the invention.

Receptor Binding

Figure 8:
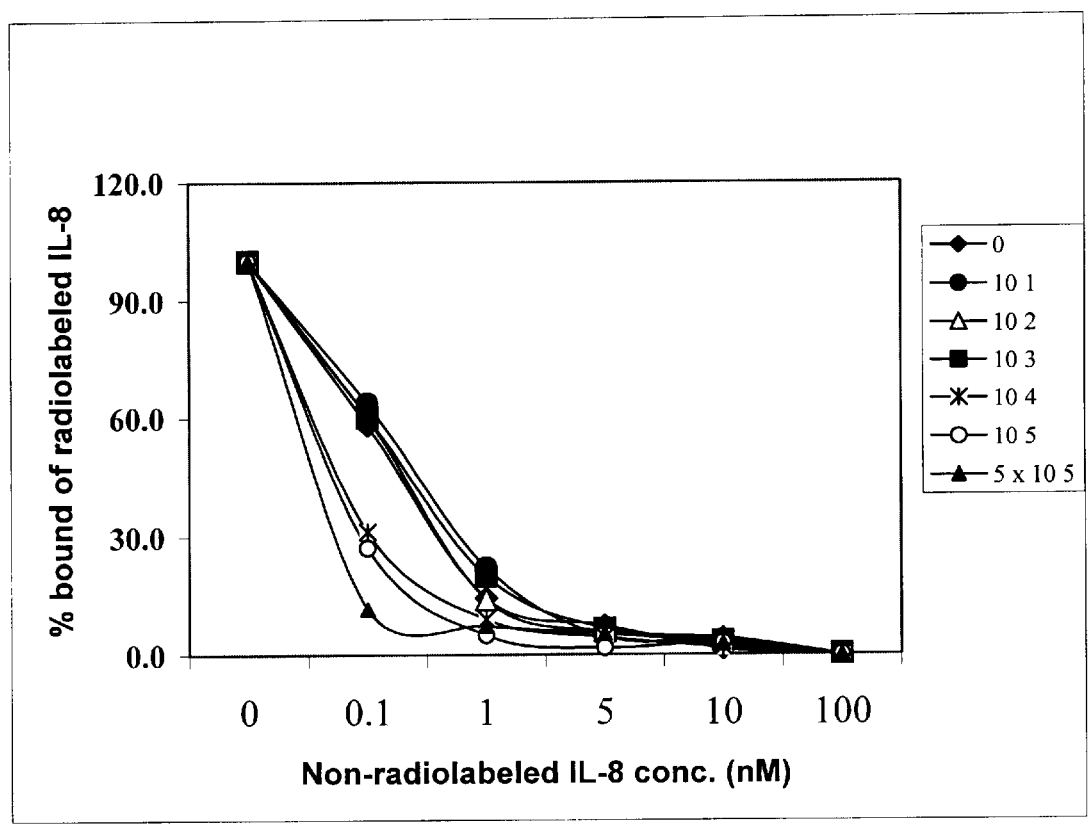
FIG. 8 shows the inhibitory effect of phenanthrene-9,10-dione on the binding of IL-8 to CXCR-1 and CXCR-2 receptors.

This example discloses the ability of tricyclic compounds of the invention, such as phenanthrene-9,10-dione (compound 1), for inhibiting binding to the MCP-1 receptor (CCR-2). The binding studies were conducted using $I^{125}$ labeled MCP-1 as competitor. FIG. 1 shows the inhibitory effect of compound (1) to the binding of MCP-1 to CCR-2. In FIG. 1, the results of competition studies are plotted using a standard scatchard plot analysis. FIG. 8 shows the inhibitory effect of (1) to the binding of IL-8 to CXCR1 and CXCR2.

Calcium Release

FIG. 2 shows that phenenthrene-9,10-dione (1) induced a rapid, transient rise in cytoplasmic calcium concentration in THP-1 cells and T-cells, analogous to the effect of native MCP-1 in both cell types mediating the release of intracellular calcium. Fura-2,AM loaded THP-1 cells were incubated with M163 for 30 min prior to induction of $[Ca^{2+}]_i$ mobilization by 20 nM MCP-1. Cells were also evaluated in the presence of fMLP (1 mM)/cytochalasin B (0.5 mM) or M163 (600 ng/ml) as positive and negative controls respectively. A shows an absolute $[Ca^{2+}]_i$ mobilized in response to the illustrated conditions. B shows relative effects of increasing M163 concentration on MCP-1 associated induction of $[Ca^{2+}]_i$ mobilization where the maximum increase of $[Ca^{2+}]_i$ mobilization was set to 100%. The $IC_{50}$ was evaluated at 250 ng/ml (120 nM). The values represent the mean +/− one S.D.

Figure 9:
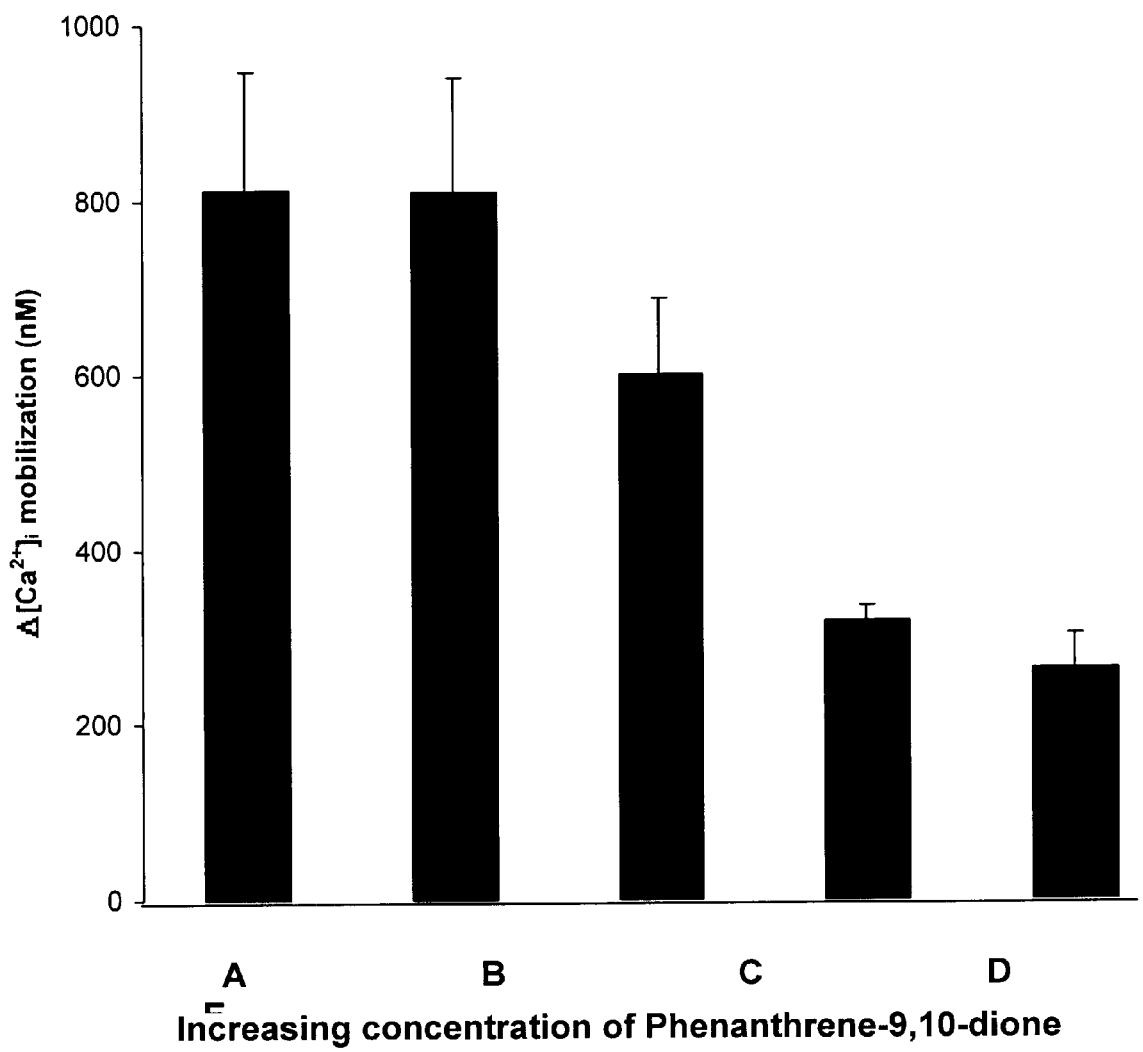
FIG. 9 shows inhibition effect of phenanthrene-9,10-dione on IL-8 induced $[Ca^{+2}]_i$ mobilization.

FIG. 9 shows the inhibition of IL-8 induced $[Ca^{2+}]_i$ mobilization by phenanthrene-9,10-dione in human neutrophils. Freshly isolated neutrophils loaded with Fura-2,AM were incubated with phenanthrene-9,10-dione for 30 minutes prior to induction of $[Ca^{2+}]_i$ mobilization by 10 nM IL-8. Values represent the increase in mobilization over basal levels (wavelength averaging at approximately 176 nM) and are the mean +/− one S.D. of n=3 experiments. Result clearly indicate that phenanthrene-9,10-dione was suppressing the calcium level about 63% at the concentration of 3 $\mu$M ($IC_{50}$ 3 $\mu$M).

In-vivo Studies Using Mouse EAE Model

Figure 3:
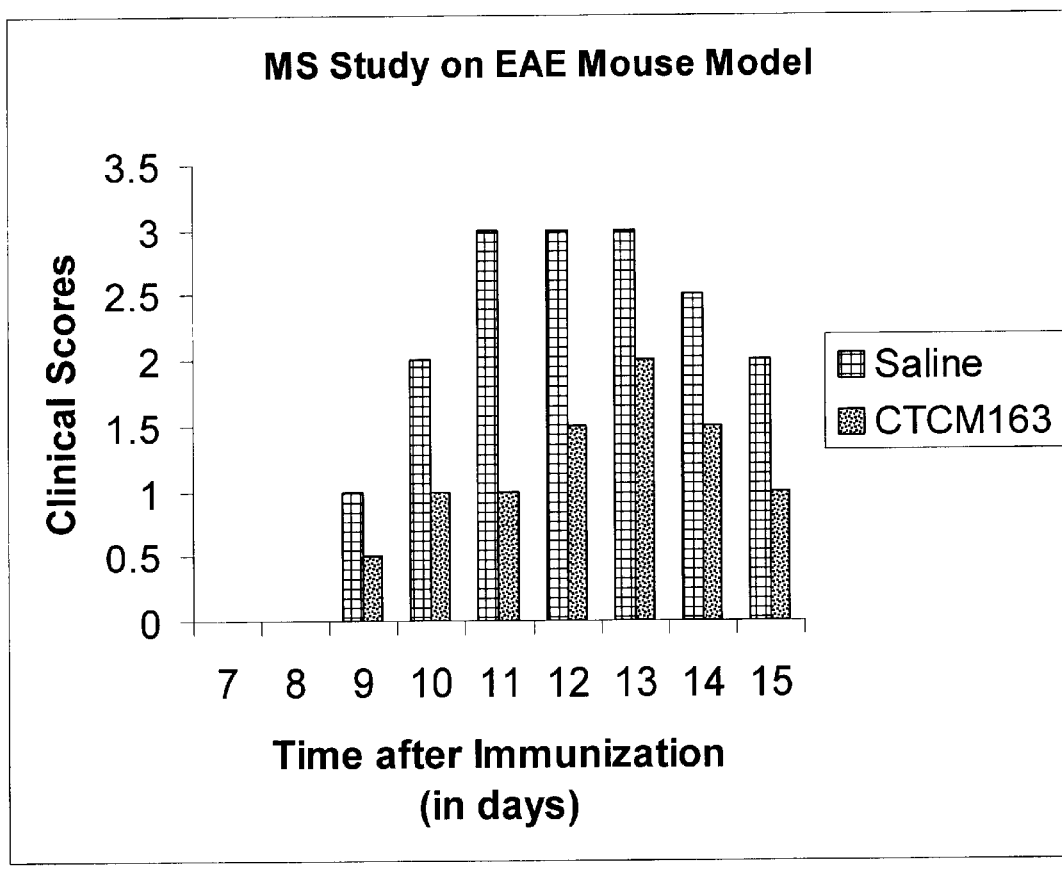
FIG. 3 shows the therapeutic effect of phenanthrene-9,10-dione (CTCM163) in the EAE mouse model of Multiple Sclerosis.

Experimental autoimmune encephalomyelitis (EAE) is a $CD4^+$ Th1-mediated inflammatory demyelinating disease of the central nervous system (CNS) that serves as a model for multiple sclerosis. It has previously been disclosed that monocyte chemotactic protein-one (MCP-1) regulates acute and relapsing autoimmune encephalomyelitis, and that MCP-1 production in the central nervous system is correlated with relapsing EAE development. In this example, the EAE mouse model for MS is used, in which the disease is induced with *Bordetella pertussis* toxin (Claude C. A. et. al., (1975) *Journal of Immunology* 114(5): 1537–1540 and Hosseimi, H. et. al., (2000) *Neurology* 54 (7): A166, An abstract presented in April 2000 on "Inhibition of proteosome prevents clinical signs in an experimental model of Multiple Sclerosis"). A dose of 1 mg/kg/day in a volume of 100 µl saline was given to animals for 14 days, and individual animals were observed daily and graded accordingly to their clinical severity as follows: grade 0, no abnormality; grade 1, limp tail; grade 2, limp tail and partial hind limb weakness; grade 3, complete hind limb paralysis; grade 4, complete hind limb paralysis and fore limb weakness; grade 5, death. FIG. 3 shows the results, which indicate that tricyclic compounds of the invention such as phenanthrene-9,10-dione has a beneficial effect on the clinical scores of the subject animals compared to a control saline injection.

CPPD and fMLP Induced Neutrophil Activation

The inflammatory diseases known as acute gouty arthritis and acute pseudogout results from the deposition of monosodium urate monohydrate (MSUM) and Calcium pyrophosphate dihydrate (CPPD) [monoclinic (M) and triclinic (T)] crystals in the synovial joints of humans (Jackson et. al., (1997) *The Journal of Rheumatology* 24(2) 341–348). In the synovial fluid (SF) the crystals become coated with numerous proteins, including opsonizing species such as IgG and complement components (McCarty; Pathogenesis and treatment of crystal-induced inflammation. In: McCarty D J ed. (1985) *Arthritis and Allied Conditions*. Philadelphia: Lea and Febiger 1495–1514). The interaction of P=protein coated crystals with neutrophils results in neutrophil respiratory burst activity, the generation of reactive oxygen species, degranulation and crystal phagocytosis (McCarty; Pathogenesis and treatment of crystal-induced inflammation. In: McCarty D J (1985) ed. *Arthritis and Allied conditions*. Philadelphia: Lea and Febiger 1495–1514).

Figure 4:
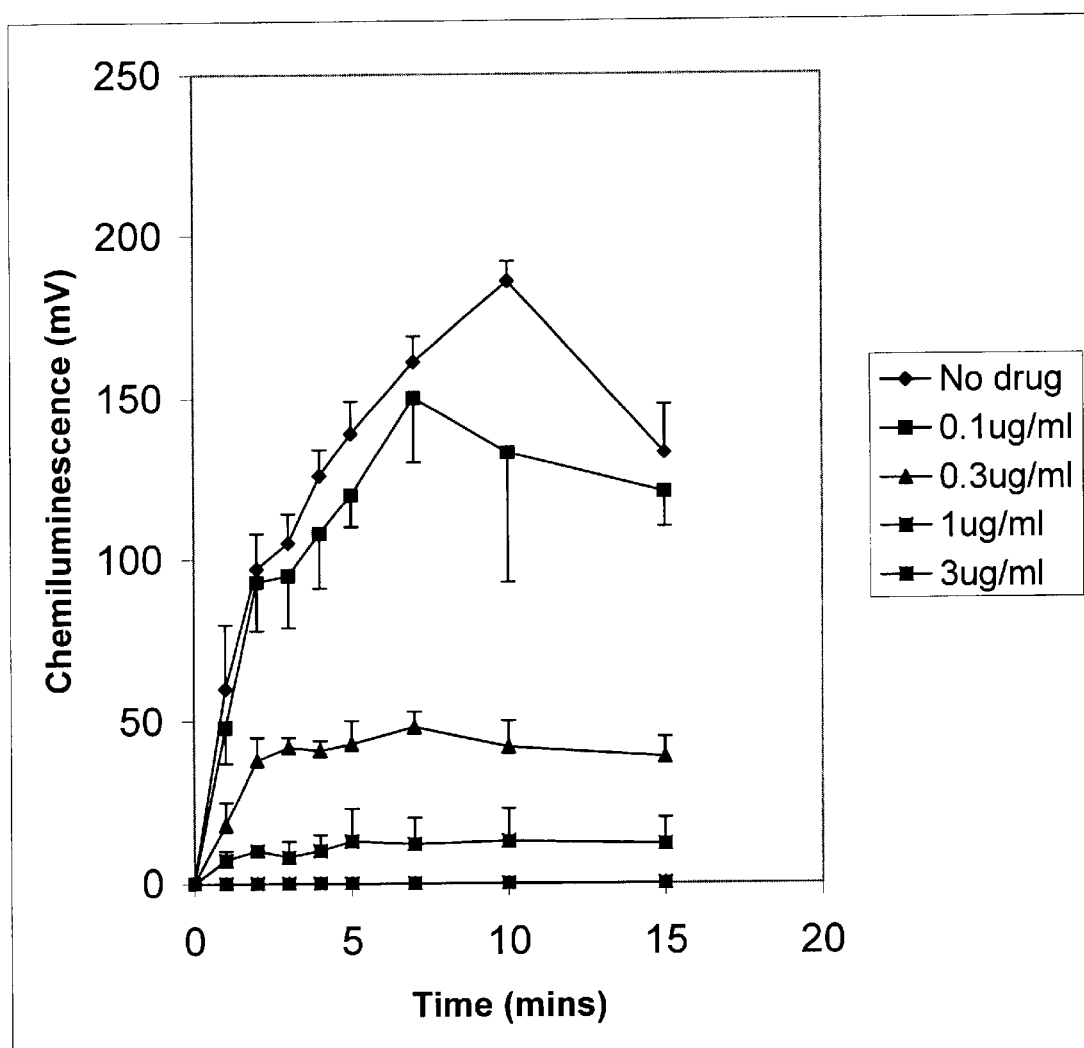
FIG. 4 shows the effect of phenanthrene-9,10-dione at various concentrations on CPPD crystal induced neutrophil activation as measured by chemiluminescence.
Figure 5:
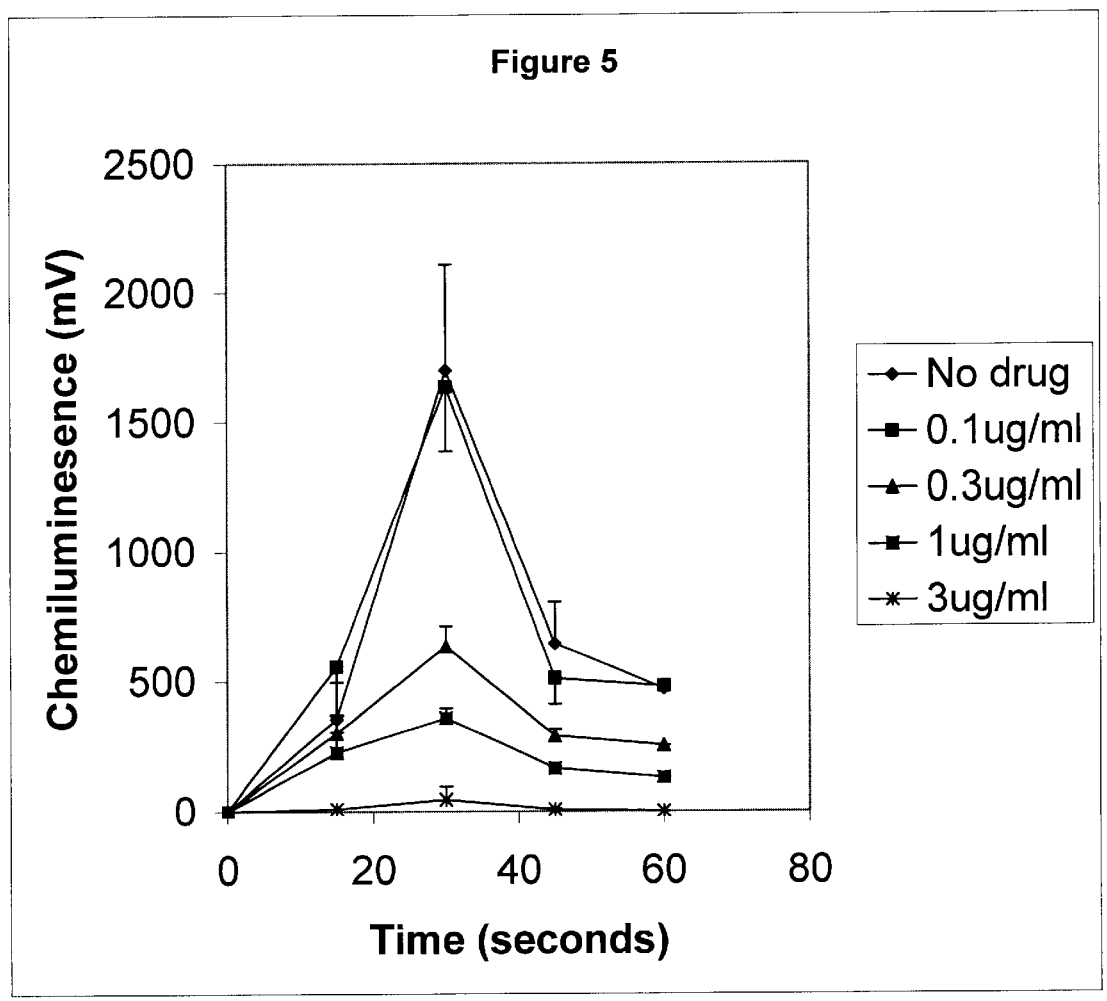
FIG. 5 shows the effect of phenanthrene-9,10-dione at various concentrations on fMLP induced neutrophil activation as measured by chemiluminescence.
Figure 6:
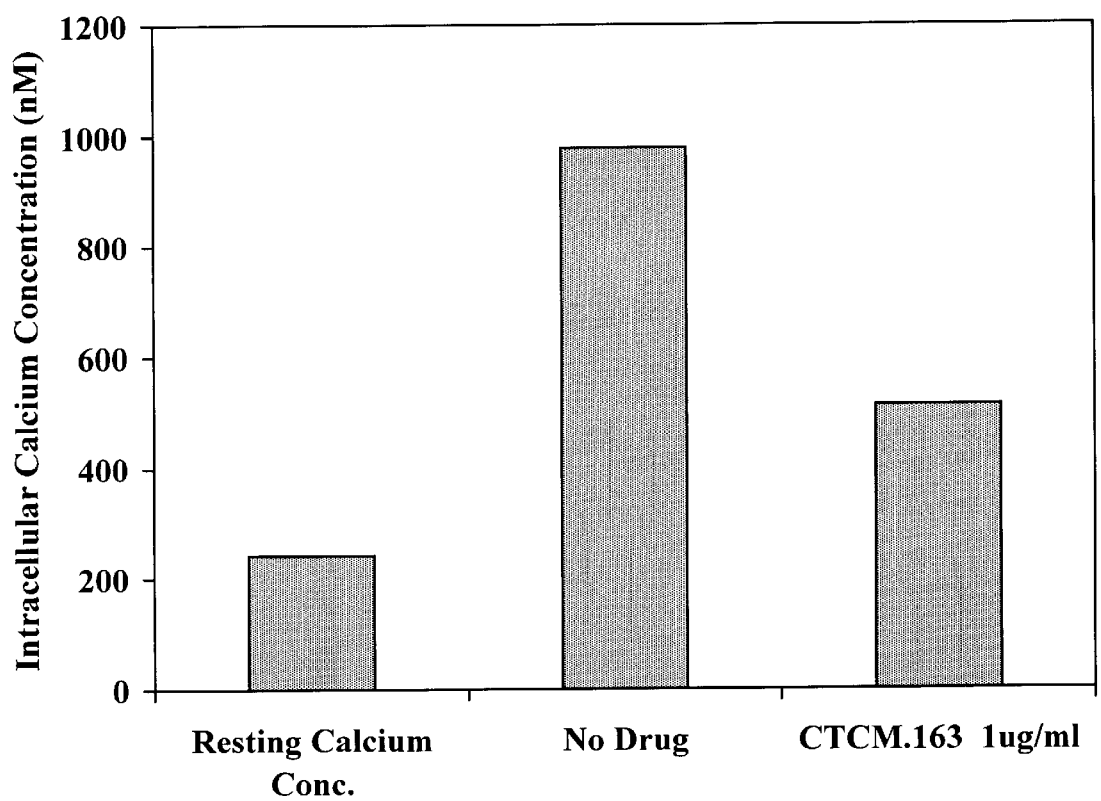
FIG. 6 shows the effect of phenanthrene-9,10-dione on fMLP Induced neutrophil calcium level, showing intracellular calcium concentration (nM) after 15 seconds stimulation.

FIG. 4 shows the effect of phenanthrene-9,10-dione at various concentrations on CPPD crystal induced neutrophil activation as measured by chemiluminescence. FIG. 5 shows the effect of phenanthrene-9,10-dione at various concentrations on fMLP induced neutrophil activation as measured by chemiluminescence. FIG. 6 shows the effect of phenanthrene-9,10-dione on fMLP Induced neutrophil calcium level. It shows that phenanthrene-9,10-dione is an effective inhibitor of intracellular calcium ion release.

Neutrophil activation by FMLP (N-formyl-methionyl-leucyl-phenylalanine) involves increases in tyrosine phosphorylation with Pttern that is reported to be different from crystal induced effect (Naccache PH et. al., (1993) Inhibition of tyrosine phosphorylation by wortmannin in human neutrophils. *Lab Invest.* 69, 19–23 and Gaundry et. al., (1993) Inflammatory microcrystals induce a distinct pattern of tyrosine phosphorylation in human neutrophils. *Journal of Clinical Investigation* 91, 1649–1655), activation of G-protein, generation of IP$_3$, increase in [Ca$^{2+}$]$_i$, activation of protein kinase C, and the subsequent assembly of the NADPH oxidase system and respiratory burst activity (Christianson et. al., (1990) *Journal of Leukocyte Biology* 47, 60–63 and Liang et. al., (1990) *Journal fo Cell Physiology* 145, 295–302).

Polymorphonuclear leukocytes (PMN) are one of the host's defense mechanisms against foreign pathogens (Dunican, A. L. et. al., (2000) *Shock* 13(3): 244–250). Typically, they are recruited to sites of inflammation to kill bacteria through release of reactive oxygen species, digestive enzymes, and phagocytosis (Root, R. K. and Cohen, M. S. (1981) *Rev. Infect Dis.* 3: 565–592 and Babior, B. M. (1978) *N. Engl. J. Med.* 298: 659–668). However, under certain conditions neutrophils can be sequestered to the lung during shock states where no exposure to subsequent stimuli, i.e., a 'second hit', they release their reactive oxygen intermediates and proteolytic enzymes causing damage to normal tissues (Thorne, J. et. al., (1989) *J. Trauma* 49: 451–456 and Tanaka, H. et. al., (1991) *Ann. Surg.* 213: 81–85). Thus, understanding how and why, otherwise normal neutrophils are recruited to sites of inflammation by chemotactic peptides, which mediate shape change, phagocytosis, and prolong neutrophil half-life, is paramount to understanding how PMN may contribute to ARDS.

FIG. 5 shows the effect of phenanthrene-9,10-dione at various concentrations on fMLP induced neutrophil activation as measured by chemiluminescence. FIG. 6 shows the effect of phenanthrene-9,10-dione on fMLP Induced neutrophil calcium level. It shows that phenanthrene-9,10-dione is an effective inhibitor of intracellular calcium ion release.

Phenanthrene-9,10-dione showed strong inhibition of both CPPD crystal and fMLP induced neutrophil activation at the concentration of 0.3 µg/ml and 1 µg/ml. In accordance with this aspect of the invention, tricyclic comounds such as phenanthrene-9,10-dione or corresponding salts may be used for the treatment of inflammatory diseases related to gout and arthritis.

Figure 7:
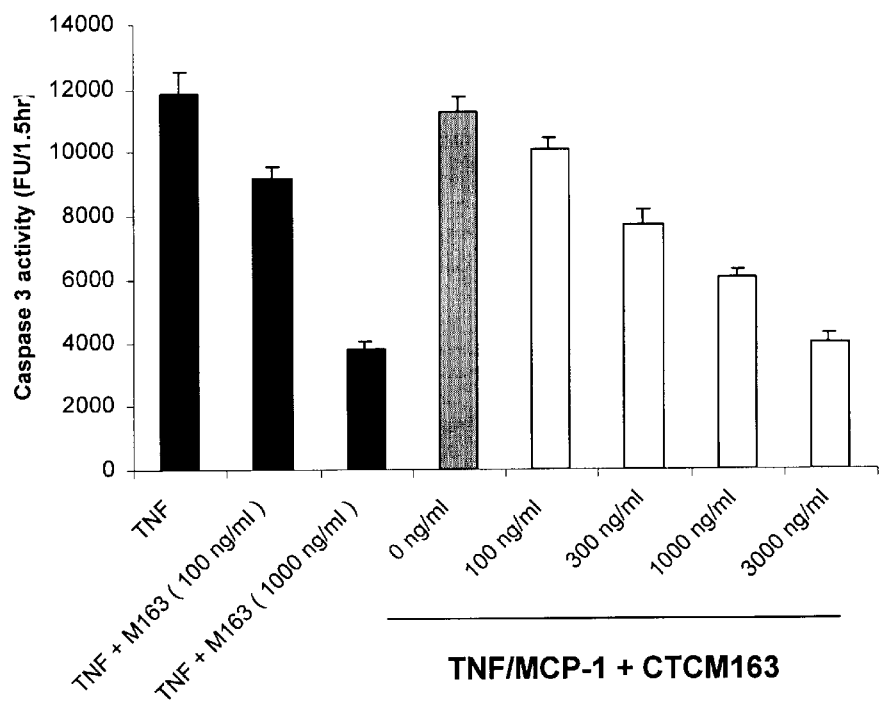
FIG. 7 shows the effect of phenanthrene-9,10-dione (CTCM 163) on TNF-α-induced caspase-3 activity in human neutrophils by fluorometric analysis.
Figure 10:
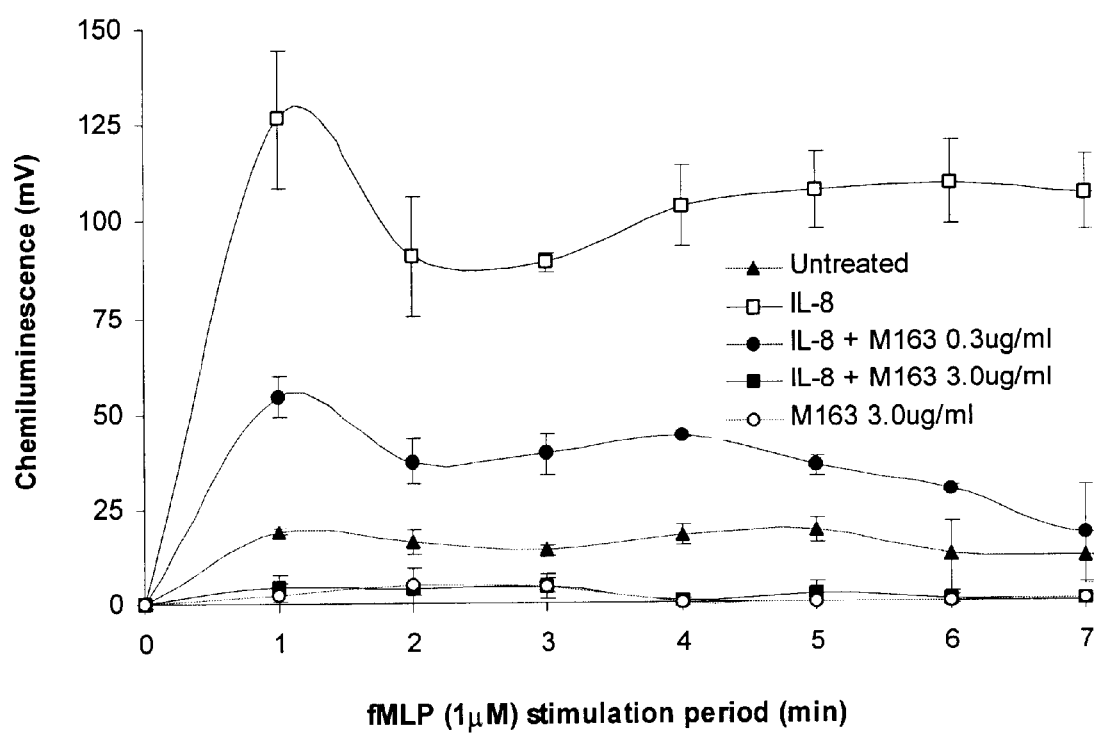
FIG. 10 shows the effect of phenanthrene-9,10-dione at various concentrations on fMLP crystal induced neutrophil activation.
Figure 11:
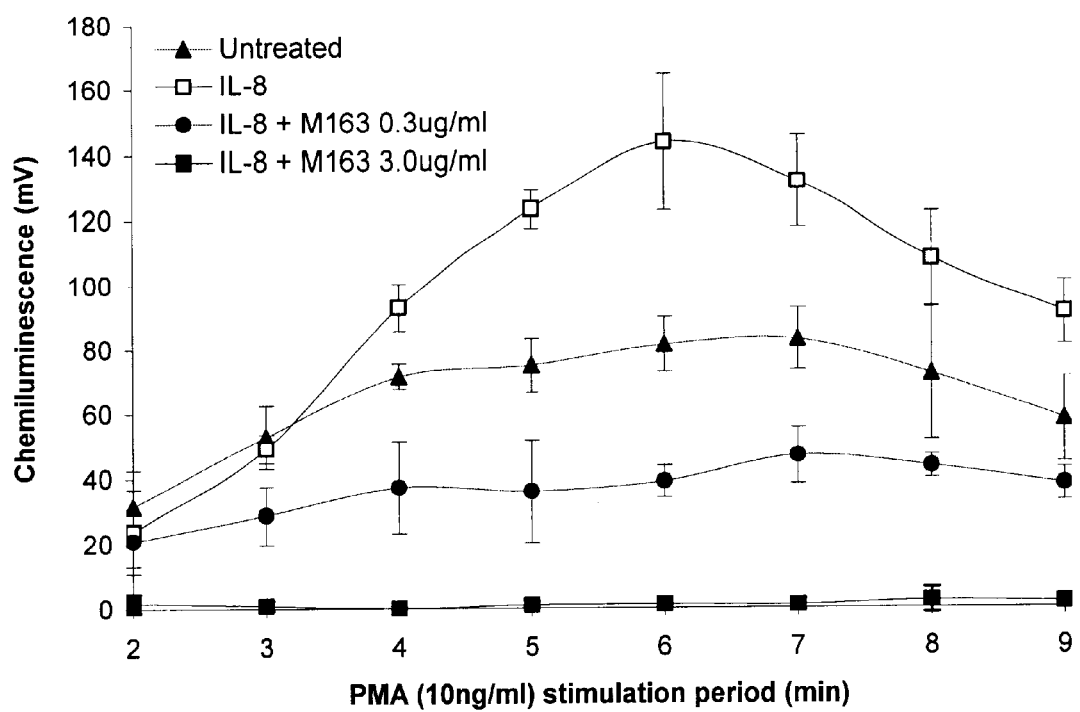
FIG. 11 shows the effect of phenanthrene-9,10-dione at various concentrations on the IL-8 priming effect on PMA crystal induced neutrophil activation as measured by chemiluminescence.

FIGS. 10 and 11 shows the effect of phenanthrene-9,10-dione on IL-8 priming effect on fMLP (1 µM) or PMA (10 ng/ml) induced human neutrophil activation, respectively. Freshly isolated human neutrophils were cultured for 24 hr alone, or in the presence of IL-8 (10 nM) with or without phenanthrene-9,10-dione (3.0 and 0.3 mg/ml) at a concentration of 2.5×10$^6$/ml. Chemiluminescence was determined in the presence of Luminol following stimulation with formyl-Met-Leu-Phe (fMLP, 1 mM) (FIG. 10) or the PKC-specific agonist phorbol 12-myristate 13-acetate (PMA, 10 ng/ml) (FIG. 11). Data are expressed as the mean +/- one S.D. for n=3 experiments Effect on TNF-α-Induced Caspase-3 Activity in Human Neutrophils Any significant delay in neutrophil apoptosis can lead to excessive accumulation and damage to surrounding tissues. Tumor necrosis factor-alpha (TNF-α) has been shown to induce extensive apoptosis in neutrophils within three hours. This invention provides an effect of phenanthrene-9,10-dione (1) on TNF-α-induced caspase 3 activity in human neutrophils by fluorometric analysis (FIG. 7). Cytoplasmic lysates were prepared from freshly isolated human neutrophils that were stimulated with 10 ng/ml TNF-α in the presence or absence of MCP-1 (100 ng/ml) for 3-hr with or without a 15 min per-incubation with M163 at the concentration indicated. DEVD-AMC specific activity was determined with or without the presence of the caspase 3 inhibitor tetrapeptide DEVD-CHO. Results are shown as the fluorometric Units (FU) of DEVD-AMC cleavage in 1.5-hr after subtracting the FU found in the presence of DEVD-CHO, and represent the mean +/- SD of n=3 experiments.

Therapeutic Formulations

In one aspect, the invention provides a variety of therapeutic uses for tricyclic compounds, such as phenanthrene-9,10-dione. In various embodiments, the compounds of the invention may be used therapeutically in formulations or medicaments for the treatment of CCR-2 mediated diseases. The invention provides corresponding methods of medical treatment, in which a therapeutic dose of a compound of the invention is administered in a pharmacologically acceptable formulation. Accordingly, the invention also provides therapeutic compositions comprising compounds of the invention and a pharmacologically acceptable excipient or carrier. The therapeutic composition may be soluble in an aqueous solution at a physiologically acceptable pH.

The invention provides pharmaceutical compositions (medicaments) containing (comprising) compound of the invention. In one embodiment, such compositions include compound of the invention in an effective amount, meaning a therapeutically or prophylactically effective amount, sufficient to modulate CCR-2 activity, and a pharmaceutically acceptable carrier. In other embodiments, the compositions of the invention may include compound of the invention in a therapeutically or prophylactically effective amount sufficient to modulate the activity of MCP-1, and a pharmaceutically acceptable carrier. Compounds of the invention may also be used in combination with other compositions and procedures for the treatment of diseases.

A "therapeutically effective amount" refers to an amount effective, at dosages and for periods of time necessary, to achieve the desired therapeutic result, such as modulation of CCR-2 or MCP1 activity. A therapeutically effective amount of a compound of the invention may vary according to factors such as the disease state, age, sex, and weight of the individual, and the ability of compounds of the invention to elicit a desired response in the individual. Dosage regimens may be adjusted to provide the optimum therapeutic response. A therapeutically effective amount is also one in which any toxic or detrimental effects of compounds of the invention are outweighed by the therapeutically beneficial effects.

A "prophylactically effective amount" refers to an amount effective, at dosages and for periods of time necessary, to achieve the desired prophylactic result, such as modulation of CCR-2 or MCP-1 activity. A prophylactically effective amount can be determined as described above for the therapeutically effective amount. Typically, since a prophylactic dose is used in subjects prior to or at an earlier stage of disease, the prophylactically effective amount will be less than the therapeutically effective amount.

In particular embodiments, a preferred range for therapeutically or prophylactically effective amounts of compounds of the invention may be 0.1 nM–0.1M, 0.1 nM–0.05M, 0.05 nM–15 $\mu$M or 0.01 nM–10 $\mu$M. Alternatively, total daily dose may range from about 0.001 to about 1 mg/kg of patients body mass. Dosage values may vary with the severity of the condition to be alleviated. It is to be further understood that for any particular subject, specific dosage regimens should be adjusted over time according to the individual need and the professional judgement of the person administering or supervising the administration of the compositions, and that dosage ranges set forth herein are exemplary only and are not intended to limit the scope or practice of the methods of the invention.

The amount of a compound of the invention in a therapeutic composition may vary according to factors such as the disease state, age, sex, and weight of the individual. Dosage regimens may be adjusted to provide the optimum therapeutic response. For example, a single bolus may be administered, several divided doses may be administered over time or the dose may be proportionally reduced or increased as indicated by the exigencies of the therapeutic situation. It is especially advantageous to formulate parenteral compositions in dosage unit form for ease of administration and uniformity of dosage. Dosage unit form as used herein refers to physically discrete units suited as unitary dosages; each unit containing a predetermined quantity of active compound calculated to produce the desired therapeutic effect in association with the required pharmaceutical carrier. The specification for the dosage unit forms of the invention are dictated by and directly dependent on (a) the unique characteristics of the active compound and the particular therapeutic effect to be achieved, and (b) the limitations inherent in the art of compounding such an active compound for the treatment of sensitivity in individuals.

As used herein "pharmaceutically acceptable carrier" or "excipient" includes any and all solvents, dispersion media, coatings, antibacterial and antifungal agents, isotonic and absorption delaying agents, and the like that are physiologically compatible. In one embodiment, the carrier is suitable for parenteral administration. Alternatively, the carrier can be suitable for intravenous, intraperitoneal, intramuscular, sublingual or oral administration. Pharmaceutically acceptable carriers include sterile aqueous solutions or dispersions and sterile powders for the extemporaneous preparation of sterile injectable solutions or dispersion. The use of such media and agents for pharmaceutically active substances is well known in the art. Except insofar as any conventional media or agent is incompatible with the active compound, use thereof in the pharmaceutical compositions of the invention is contemplated. Supplementary active compounds can also be incorporated into the compositions.

Therapeutic compositions typically must be sterile and stable under the conditions of manufacture and storage. The composition can be formulated as a solution, microemulsion, liposome, or other ordered structure suitable to high drug concentration. The carrier can be a solvent or dispersion medium containing, for example, water, ethanol, polyol (for example, glycerol, propylene glycol, and liquid polyethylene glycol, and the like), and suitable mixtures thereof. The proper fluidity can be maintained, for example, by the use of a coating such as lecithin, by the maintenance of the required particle size in the case of dispersion and by the use of surfactants. In many cases, it will be preferable to include isotonic agents, for example, sugars, polyalcohols such as mannitol, sorbitol, or sodium chloride in the composition. Prolonged absorption of the injectable compositions can be brought about by including in the composition an agent which delays absorption, for example, monostearate salts and gelatin. Moreover, compounds of the invention can be administered in a time release formulation, for example in a composition which includes a slow release polymer. The active compounds can be prepared with carriers that will protect the compound against rapid release, such as a controlled release formulation, including implants and microencapsulated delivery systems. Biodegradable, biocompatible polymers can be used, such as ethylene vinyl acetate, polyanhydrides, polyglycolic acid, collagen, polyorthoesters, polylactic acid and polylactic, polyglycolic copolymers (PLG). Many methods for the preparation of such formulations are patented or generally known to those skilled in the art.

Sterile injectable solutions can be prepared by incorporating compounds of the invention in the required amount in an appropriate solvent with one or a combination of ingredients enumerated above, as required, followed by filtered sterilization. Generally, dispersions are prepared by incorporating the active compound into a sterile vehicle which contains a basic dispersion medium and the required other ingredients from those enumerated above. In the case of sterile powders for the preparation of sterile injectable solutions, the preferred methods of preparation are vacuum drying and freeze-drying which yields a powder of the active ingredient plus any additional desired ingredient from a previously sterile-filtered solution thereof. In accordance with an alternative aspect of the invention, compounds of the invention may be formulated with one or more additional compounds that enhance the solubility of compounds of the invention.

Pharmaceutically acceptable salts include salts that are well known to those skilled in the art such as basic salts of inorganic and organic acids, such as hydrochloric acid, hydrobromic acid, sulphuric acid, phosphoric acid, methane sulphonic acid, ethane sulphonic acid, acetic acid, malic acid, tartaric acid, citric acid, lactic acid, oxalic acid, succinic acid, fumaric acid, maleic acid, benzoic acid, alicylic acid, phenylacetic acid and mandelic acid. In alternative embodiments, pharmaceutically acceptable cation salts may include alkaline, alkaline earth, ammonium and quaternary ammonium cations.

In accordance with another aspect of the invention, therapeutic compositions of the present invention, comprising compounds of the invention, may be provided in containers having labels that provide instructions for use of compounds of the invention to treat chemokine or chemokine receptor mediated diseases, inflammation, acute inflammation, chronic inflammation, atherosclerosis, psoriasis, gout, acute pseudogout, acute gouty arthritis, arthritis, rheumatoid arthritis, allograft rejection, chronic transplant rejection, asthma, stroke, mononuclear-phagocyte dependent lung injury, idiopathic pulmonary fibrosis, sarcoidosis, focal ischemia, autoimmune encephalomyelitis, multiple sclerosis, atopic dermatitis, asthma, chronic obstructive pulmonary disease, adult respiratory distress syndrome, inflammatory bowel disease. Crohn's disease, ulcerative colitis, septic shock, endotoxic shock, gram negative sepsis, toxic shock syndrome, cardiac and renal reperfusion injury, glomerulonephritis, thrombosis, graft vs. host reaction, alzheimers disease, allograft rejections, malaria, restinosis, and angiogenesis.

Conclusion

Although various embodiments of the invention are disclosed herein, many adaptations and modifications may be made within the scope of the invention in accordance with the common general knowledge of those skilled in this art. Such modifications include the substitution of known equivalents for any aspect of the invention in order to achieve the same result in substantially the same way. Numeric ranges are inclusive of the numbers defining the range. In the specification, the word "comprising" is used as an open-ended term, substantially equivalent to the phrase "including, but not limited to", and the word "comprises" has a corresponding meaning. Citation of references herein shall not be construed as an admission that such references are prior art to the present invention. All publications, including but not limited to patents and patent applications, cited in this specification are incorporated herein by reference as if each individual publication were specifically and individually indicated to be incorporated by reference herein and as though fully set forth herein.

What is claimed is:

1. A method of modulating the activity of a chemokine in a host, comprising administering to the host an effective amount of a compound of formula (I), or a pharmaceutically acceptable salt thereof:

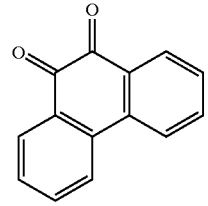

wherein the chemokine is chosen from IL-8, MCP-1, and chemokines that bind to a chemokine receptor in a mammal chosen from CXCR-1, CXCR-2, CCR-2 and CCR-4 wherein the compounds binds to the chemokine receptor with a binding affinity below 100 nm.

2. A method of inhibiting the interaction of a chemokine with a chemokine receptor in a mammal, comprising administering to the mammal an effective amount of a compound of formula or a pharmaceutically acceptable salt thereof:

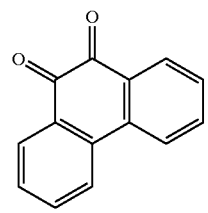

wherein the chemokine is chosen from IL-8, MCP-1, and chemokines that bind to a chemokine receptor in a mammal chosen from CXCR-1, CXCR-2, CCR-2, and CCR4 wherein the compound binds to the chemokine receptor with a binding affinity below 100 nM.

3. A method of treating multiple sclerosis in a mammal in need of such treatment, which comprises administering to the mammal an effective amount of a compound of the formula or a pharmaceutically acceptable salt thereof:

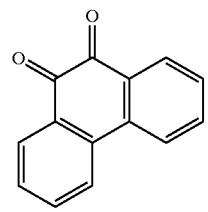

wherein the chemokine is chosen from IL-8, MCP-1, and chemokines that bind to a chemokine receptor in a mammal chosen from CXCR-1, CXCR-2, CCR-2 and CCR-4.

4. The method of claim 3, wherein the compound binds to the chemokine receptor with a binding affinity below 100 nM.

* * * * *